(12) United States Patent
Lynn

(10) Patent No.: US 8,361,408 B2
(45) Date of Patent: *Jan. 29, 2013

(54) LUER PROTECTION POUCH AND LUER VALVE/MALE LUER PROTECTION METHOD

(76) Inventor: Lawrence Allan Lynn, Delaware, OH (US)

( * ) Notice: Subject to any disclaimer, the term of this patent is extended or adjusted under 35 U.S.C. 154(b) by 137 days.

This patent is subject to a terminal disclaimer.

(21) Appl. No.: 12/807,737

(22) Filed: Sep. 13, 2010

(65) Prior Publication Data

US 2011/0125104 A1    May 26, 2011

Related U.S. Application Data

(63) Continuation-in-part of application No. 11/724,888, filed on Mar. 16, 2007, now Pat. No. 7,794,675, and a continuation-in-part of application No. 11/801,649, filed on May 10, 2007, and a continuation-in-part of application No. 11/805,381, filed on May 23, 2007.

(Continued)

(51) Int. Cl.
  *A61L 2/00*   (2006.01)
  *A61L 9/00*   (2006.01)
  *A61L 2/18*   (2006.01)

(52) U.S. Cl. ............... 422/294; 422/292; 422/28

(58) Field of Classification Search ......... 422/292, 422/294, 28; 604/263
  See application file for complete search history.

(56) References Cited

U.S. PATENT DOCUMENTS

| | | | |
|---|---|---|---|
| 2,999,260 A | 9/1961 | King | |
| 3,103,029 A | 9/1963 | Valles | |
| 3,183,543 A | 5/1965 | Worcester | |
| 3,240,326 A | 3/1966 | Miller | |
| 3,450,129 A * | 6/1969 | Brewer et al. | 600/572 |
| 3,903,345 A | 9/1975 | Baker et al. | |
| 3,945,380 A * | 3/1976 | Dabney et al. | 604/410 |
| 4,243,035 A | 1/1981 | Barrett | |
| 4,440,207 A | 4/1984 | Genatempo et al. | |
| 4,725,267 A | 2/1988 | Vaillancourt | |
| 5,088,146 A | 2/1992 | Smith et al. | |
| 5,190,534 A | 3/1993 | Kendell | |

(Continued)

FOREIGN PATENT DOCUMENTS

CA  25 47 485   11/2006
DE  25 54 589   6/1976

(Continued)

OTHER PUBLICATIONS

International Search Report and Written Opinion of the International Searching Authority mailed Oct. 1, 2008 in PCT/US08/06039 which corresponds to U.S. Appl. No. 11/801,649.

(Continued)

*Primary Examiner* — Regina M. Yoo
(74) *Attorney, Agent, or Firm* — Banner & Witcoff, Ltd

(57) ABSTRACT

A medical swab pouch is disclosed. The inexpensive elastic pouch contains disinfectant and is configured for protecting and swabbing a wide variety of luer systems to prevent and eliminate bacterial contamination. The pouch has a flattened configuration and can be elastically dilated, as by squeezing the pouch between the thumb and index finger and is readily carried in large numbers in nurse's pockets (in a manner similar to that for conventional alcohol swabs). The pouch covers and protects the luer valve at the discretion of the user and without transmission of torsion or longitudinal force which might loosen the luer valve or otherwise be transmitted to the vein.

20 Claims, 31 Drawing Sheets

Related U.S. Application Data

(60) Provisional application No. 60/782,913, filed on Mar. 16, 2006, provisional application No. 60/836,637, filed on Aug. 9, 2006, provisional application No. 60/900,536, filed on Feb. 8, 2007.

(56) References Cited

U.S. PATENT DOCUMENTS

| | | | |
|---|---|---|---|
| 5,242,425 A | 9/1993 | White et al. | |
| D342,134 S | 12/1993 | Mongeon | |
| 5,433,705 A | 7/1995 | Giebel et al. | |
| 5,554,135 A | 9/1996 | Menyhay | |
| 5,580,530 A * | 12/1996 | Kowatsch et al. | 422/559 |
| 5,733,503 A * | 3/1998 | Kowatsch et al. | 422/28 |
| 5,964,785 A * | 10/1999 | Desecki et al. | 604/523 |
| 6,045,539 A | 4/2000 | Menyhay | |
| 6,677,258 B2 | 1/2004 | Carroll et al. | |
| 6,753,306 B2 | 6/2004 | Simpson | |
| 6,893,428 B2 | 5/2005 | Willemstyn | |
| 7,127,771 B2 | 10/2006 | McDevitt et al. | |
| 7,214,214 B2 | 5/2007 | Sudo et al. | |
| 7,316,669 B2 | 1/2008 | Ranalletta | |
| 7,794,675 B2 * | 9/2010 | Lynn | 422/294 |
| 7,932,099 B2 * | 4/2011 | Egan et al. | 436/514 |
| 2002/0183229 A1 | 12/2002 | Simpson | |
| 2002/0197738 A1 * | 12/2002 | Matsumoto et al. | 436/518 |
| 2003/0026729 A1 * | 2/2003 | Wu et al. | 422/33 |
| 2005/0115856 A1 * | 6/2005 | Halkyard | 206/494 |
| 2005/0124709 A1 | 6/2005 | Krueger et al. | |
| 2007/0093762 A1 | 4/2007 | Utterberg et al. | |
| 2007/0112333 A1 * | 5/2007 | Hoang et al. | 604/533 |
| 2007/0185383 A1 * | 8/2007 | Mulhern et al. | 600/121 |
| 2007/0225660 A1 | 9/2007 | Lynn | |
| 2008/0019889 A1 * | 1/2008 | Rogers et al. | 422/292 |
| 2008/0038167 A1 * | 2/2008 | Lynn | 422/294 |
| 2008/0039803 A1 | 2/2008 | Lynn | |
| 2008/0086091 A1 | 4/2008 | Anderson et al. | |
| 2008/0177250 A1 | 7/2008 | Howlett et al. | |
| 2008/0199851 A1 * | 8/2008 | Egan et al. | 435/5 |
| 2009/0008393 A1 | 1/2009 | Howlett et al. | |
| 2009/0028750 A1 | 1/2009 | Ryan | |
| 2009/0041619 A1 | 2/2009 | Cady et al. | |
| 2009/0062766 A1 | 3/2009 | Howlett et al. | |
| 2010/0292673 A1 * | 11/2010 | Korogi et al. | 604/533 |
| 2011/0236879 A1 * | 9/2011 | Egan et al. | 435/5 |

FOREIGN PATENT DOCUMENTS

| | | |
|---|---|---|
| DE | 25 54 588 | 2/1977 |
| GB | 1 596 620 | 8/1981 |

OTHER PUBLICATIONS

Photographs of a prior art plastic flip cap for covering a septum of an arterial line.
Photographs of a prior art thin flexible plastic finger nail cover.
Images and/or description of conventional alcohol swab packages and lens cleaner.
Extended European Search Report issued in related European Application No. 08754365.8, dated Oct. 29, 2012, which corresponds to PCT/US2008/006039 and U.S. Appl. No. 11/801,649.

* cited by examiner

Prior Art (Piston Luer Valve)

Prior Art (Piston Luer Valves)

Fig. 46
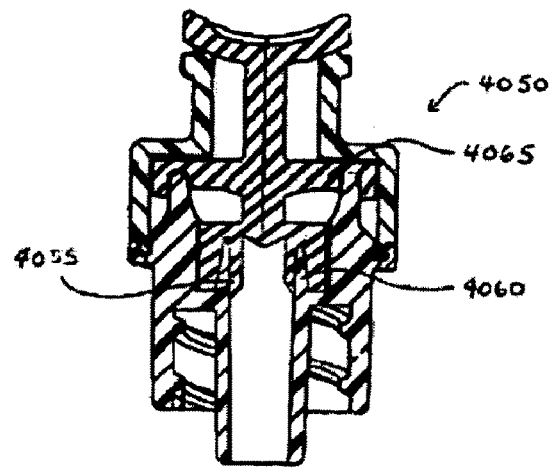
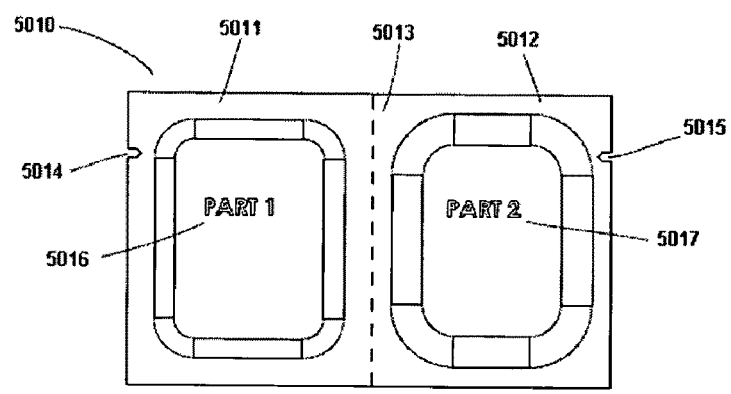
Figure 47
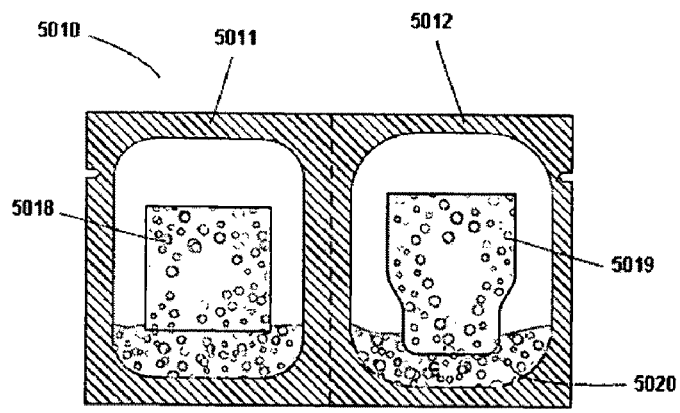
Figure 48

LUER PROTECTION POUCH AND LUER VALVE/MALE LUER PROTECTION METHOD

CROSS-REFERENCE TO RELATED APPLICATIONS

This application is a Continuation-in-part of U.S. Patent Application Ser. No. 11/724,888 filed Mar. 16, 2007 now U.S. Pat. No. 7,794,675, U.S. Patent Application Ser. No. 11/801,649 filed May 10, 2007 and U.S. Patent Application Ser. No. 11/805,381 filed May 23, 2007 which claim priority of Provisional Application 60/782,913 filed Mar. 16, 2006, Provisional Application 60/836,637, filed Aug. 9, 2006, and Provisional Application 60/900,536, filed Feb. 8, 2007 the contents of each of which are incorporated by reference as if completely disclosed herein.

BACKGROUND AND SUMMARY OF THE INVENTION

Medical patient access devices and access systems allow access to the interior of the patient (such as the vascular system) to deliver a fluid or a pharmaceutical. However, the movement of potentially deadly microorganisms into patient's interior through such access devices and systems has long been a major problem. Bacteria and yeast may gain entry into a patient's vascular system from access ports during the connection of the port to deliver the fluid or pharmaceutical. In fact each access occurrence into an access portal is associated with at least some risk of comprising a "Microorganism Transmitting Event" (MTE). The bacterial or yeast bolus associated with a MTE can comprise a single organism or greater than 1000 organisms. While most MTEs are without consequence, each MTE poses a risk of causing clinical bacteremia which is associated with severe morbidity, increased hospital expense and/or death. The risk of each MTE is related to the vulnerability of the patient and the pathogenicity and sensitivity of the organism transmitted. Factors which greatly amplify the risk posed by a given MTE are a low WBC count, the presence of prosthetic heart valves or joints, and malnutrition, to name a few. Regardless of the vulnerability of the patient, once clinical bacteremia is established, the death rate is relatively high. Microorganisms are becoming more resistant to antibiotics and patients are often living longer with more prosthetic components and therefore the risk posed by MTEs to patients will likely continue to increase over the next few decades.

Throughout the sequence of procedures associated with an access event there are many risks of contact or droplet nuclei contamination which can contribute to MTEs. Contamination can occur during drug mixing, attachment of a cannula, and insertion into the access portal. Because the access procedure is so common and simple, the risk associated with entry into fluid connection with a patient's vascular system has often been overlooked. Presently the risk to hospitals and patients is a substantial function of diligence of the employee performing the accesses and this diligence is largely uncontrollable. When substantial morbid and mortal risk in association with a high number of routine procedures is defined as a primary function of the diligence of a heterogeneous population of employees, a substantial degree of unnecessary injury to patients will inevitably result The present inventor contends that it is unacceptable for hospitals to perform hundreds of thousands of accesses to patient's vascular system without controlling all of the controllable risks associated with the access procedure.

It is the purpose of the present invention to provide a system and method which allows control of the risk along that all portions of the medication mixing delivery process such that drug mixing can be performed at the bedside within a predictably sterile enclosure and patient protecting components such as the biocidal septum and cannula system with or without a antiseptic cover are used so that substantially all of the controllable risks are controlled.

One purpose of the present invention is to reduce global morbidity and mortality related to access worldwide by reducing the contamination risk associated with drug mixing, reduce the risk associated with each access, and finally to reduce the number of accesses themselves.

It is important to understand the dynamics of access related transmission events. For this purpose several useful terms will be introduced. The present inventor defines the "MTE Magnitude" as the number of transmitted organisms associated with a given MTE. The peak, the variability and distribution, and the aggregate MTE Magnitude values (such as the mean MTE Magnitude per 100 access events) are all relevant. The present inventor defines the "MTE %" as the percentage of access events which are associated with MTEs. Because access devices differ in structure and function, each access device type differs both with respect to the MTE % and at least one value indicative of the MTE Magnitude. The risk of clinical bacteremia and death due to a MTE is a direct function of 3 primary factors. The MTE Magnitude, the pathogenicity of the organisms transmitted, and the patient's state of vulnerability. Finally, the risk of severe sepsis induced morbidity and/or death due to an access device is a direct function 4 primary factors, the MTE Magnitude, the MTE %, the pathogenicity of the organisms transmitted, and the patient's state of vulnerability. The first two of those factors are exquisitely dependent on the design of the access device.

Given the complexity defining the risks associated with a given access event, the addition of new uncontrolled risk associated with a less than diligent worker in the performance of a diligence dependent access procedure is unacceptable. Since worker diligence can never be reasonably assured, it is one of the purposes of the present invention to provide a much more "diligence independent access procedure".

In many environments and medical settings cleansing immediately prior to access is not reliably performed, therefore even if it is possible to comprehensively clean an access device and thereby achieve low the MTE % and MTE Magnitude values for a given device in a carefully performed clinical trial, this approach would not reflect the likely real world impact of that access device on global mortality. In addition the effect of even a single missed cleaning event prior to access may have a greater impact on certain access device types. While a missed cleaning event prior to access may have little effect on one device type (other than perhaps to cause a single MTE event to occur during the access which occurred without the cleansing), the same single missed cleaning event may severely contaminate the interior of another device type. For example, the interstitial dead spaces of open piston valves, which is juxtaposed the fluid opening, are not accessible to cleaning. For this reason, even a single event of failure to cleanse the access surface of an open piston valve prior an access event may contaminate the incubating interstitial spaces of an open piston valve early in its use and therefore may potentially cause a rapid rise in both MTE % and MTE Magnitude as the organisms incubate inside the valve over the next 72 hours (long after the initial uncleansed access occurred). The present inventor designates this feature of some access devices as "access induced irreversible incubation". Conventional access device designs in wide use today which exhibit a functional propensity for irreversible incubation will not stand the test of time.

In the real world a mix of cleansed and uncleansed accesses commonly occur. Since cleansing is not universally practiced, a combination of both the cleansed and uncleansed MTE % and MTE Magnitude values reflect the real word risk of morbidity and death related to access. In addition the effect of early internal contamination on internal incubation and rising MTE % and MTE Magnitude should be evaluated if the true risk of a given device is to be reasonably assessed.

The present inventor proposes that the annual number of deaths worldwide associated with access devices is given by formula 1. The implications of this simple formula are profound and formula 1 should be considered carefully by every designer of access devices. $D=A_1(R_1)+A_2(R_2)\ldots +A_n(R_n)$ 1. Where: [0011] D=the number of sepsis deaths per year due to access events [0012] $A_1$=the number of accesses events per year for device 1 [0013] $R_1$=the mean risk of death per access event for device 1 [0014] n=the number of different access devices in the worldwide market $R_1$ is a direct function at least one MTE magnitude value for access device 1. Of course the value R for any access device cannot be known with the evidence available today and even for the most dangerous access devices, R will be extremely small. However, worldwide millions of access events are performed every day. For this reason very small difference in MTE % and/or MTE Magnitude between widely deployed devices can translate into major differences in access device related mortality. Perhaps the most subtle implications of formula 1 is that minor design features which subtly favor microorganism transmission or even a modestly inferior design type with exhibits the propensity for irreversible incubation may have a major impact on the access related death rate worldwide. Also because any R is vastly amplified in patients with low WBC or when the organism is highly pathogenic and resistant (such as Vancomycin Resistant *Staphlococcus Aureus*), a modestly inferior design may appear quite safe in one population but be highly dangerous to other populations.

The above relationship clearly shows that the global death rate associated with access devices can be reduced by reducing the number of access events or by developing new devices with a lower MTE % and MTE Magnitude values especially if these are low for both cleansed and uncleansed accesses. An access device which has low MTE % and MTE Magnitude values in both the cleansed and uncleansed state is described by the present inventor as comprising an "anti-infective access device". It is the one purpose of the present invention to reduce the global death rate related to access events by providing an anti-infective access device which achieves; a reduction in number of access events, a reduction in the MTE % and MTE Magnitude, less dependency on cleansing, and high resistance to irreversible contamination and incubation.

According to one aspect of the present invention an access system is provided which does not protect or incubate microorganisms in exposed regions juxtaposed the fluid path. With devices which lack this feature, such as the open piston valves (like the Clave), bacteria (and other microorganisms) often first gain access to crevices and spaces along or within the access system from environmental contamination, the healthcare worker, or from the skin or excretions of the patient. The bacteria often propagate in these crevices and spaces producing a protective biofilm. Often, portions of these residing bacteria, with or without supporting biofilm, can be displaced into the lumen of the access device. This displacement is commonly mechanical and induced by the insertion of a solid member such as a male luer into the device. Once displaced, the bacteria are then readily carried by the solid member or by fluid flow into the patient where they can cause death especially in patients with low white blood cell counts or internal prosthetic devices. Each time a conventional access device is entered from the outside the risk to the patient is increased. Typical access systems include, for example luer valves, ports, stopcocks, catheter and tubing mounted septum, hollow receivers, introducers, catheters, manifolds, hubs with extension sets, and open tubing connection systems to name a few. The term access systems is extended herein to include systems which receive a medical implement and which contain medical agents for insertion into a patient or for receipt of fluid from within a patient body such as drug vials, IV bags, pressure monitoring systems, and urinary bags to name a few. Access systems generally have interior portions for receiving medical implements, for example male luers, needles, biopsy devices, retrieval devices, catheters, and stents to name a few. Access systems also usually include at least one interior lumen to receive fluid or to store fluid.

In an example, access systems which comprise the luer receiving hubs of IV catheters and Y sites are particularly vulnerable because they may be entered with external male luers up to 10 or more times a day. Often the luer is contaminated during use but this contamination is invisible so that the luer is stored in a cap and reused. Research performed at the Center for Disease Control and Prevention clearly demonstrated that piston luer valves have internal walls, which can allow growth of vast numbers of deadly bacteria.

FIG. 1 shows a piston luer valve of the prior art with the exposed circumferential crevice into which bacteria can gain access to a region of incubation. The straight arrow points to the circumferential crevice at the face of the device, which connects directly with the internal walls of the valve (curved arrow). FIG. 3 is a photo of a pair of piston luer valves of the prior art, showing how the male luer is connected to the upper face of the piston luer valve (region of both the straight and curved arrow of FIG. 1). Once the bacteria gain access the inner surface of the piston luer valves biofilm can attach to the inner surface. To illustrate, FIG. 3 is an electron micrograph of bacteria and biofilm on the inner surface of a piston luer valve of FIG. 2 taken during a study by the Centers for Disease Control and Prevention in Atlanta Ga., (Donlan et al., Journal of Clinical Microbiology, February 2001, p. 750-753, Vol. 39, No. 2.). The article is incorporated herein by reference and provides additional background for the present invention.

The problem with at least some of the piston luer valves has become an increasingly recognized problem with published outbreaks. Indeed, when a patient in 2006 with an indwelling IV catheter develops a fever, the physician must promptly consider the piston luer valve as the potential source of the infection and replace it if there is any question as to whether or not the luer valve has been colonized internally.

Another problem relates to contamination and/or colonization of implements (such as the luer tip) between insertions into the access device. For example, during intermittent piggyback infusions, it is desirable to store the male luer in a sterile environment between uses. The problems associated with the storage of medical implements between uses are also discussed in U.S. Pat. No. 5,167,643 of the present inventor (the contents of which are incorporated by reference as if completely disclosed herein). This patent provides additional background for the present invention. Although capping and docking the luer tip can provide a component of protection from the environment, the tip end and outer sidewall of the male luer is often already contaminated with bacteria before recapping therefore the cap can actually act as an incubator. Bacteria actually can reach the luer tip from the access device itself. In fact, during use, the tip (including the outer sidewall of the tip) of the male luer as in FIG. 2 actually resides within the previously discussed circumferential crevice and adjacent the sidewall (FIG. 1) of the piston luer valve.

The present inventor has witnessed marked visible contamination of a luer tip, which was withdrawn from a open piston luer valve of the type shown in FIG. 2 in use in the intensive care unit. If this contamination had not been visible and the male luer stored in a conventional cap, this contamination might well have been displaced into the patient with the next connection. Most of the time the contaminating microorganisms are not associated with visible biofilm. So that the organisms are commonly carried directly into the caps and/or valve where they can proliferate and cause death.

Indeed, both the biofilm and the bacteria within the circumferential crevice can become attached to the male luer tip and then be carried to the site of storage (such as within a new sterile cap). In this case the interior of the new cap will now become contaminated by the outside of the male luer and the organisms can then propagate on the male luer tip and within the cap between accesses. Since caps are commonly reused and may contain fluid from the luer, the cap, which is supposed to act as a "luer protector", can actually function as an incubator for bacteria during and between connections with the access device. As is evident from this discussion, the problem is profound because the system interconnects between the implement, the cover for the implement, and the access device. Once a reservoir for bacterial growth is allowed to develop within an access device, the cover, or the medical implement itself, the organism can produce a trail of contaminating movement to all connecting components of the system.

As discussed in U.S. Pat. No. 6,171,287 of the present inventor (the contents of which are incorporated by reference as if completely disclosed herein), structural complexity as a function of spaces between internal moving parts, and especially exposed crevices which connect to internal rigid components can greatly increase the risk of colonization. However, even with the elimination of these crevices, bacteria can still invade access systems. One approach has been to add an anti-infective chemical agent to access devices as coatings, impregnations, or filling fluid. However this approach is often less than optimally effective because biofilm, indwelling fluid, or distance may protect the organism from diffusion of the agent. Also the bacteria or yeast may develop resistance to the chemical agent or the patient or an incompatible drug may react to the agent. Another approach commonly is to increase the education of the need to scrub the surface with disinfectant. Unfortunately, as is evident from a review of FIG. 1, the circumferential crevice of piston luer valves of the type discussed above is not accessible to scrubbing. Many of these types of devices are manufactured with opaque outer sidewalls hiding the circumferential crevice so even the presence of blood and other nutrients within the crevice are not visible to the healthcare worker. The outside of the device may be scrubbed and look pristine while the inside is loaded with nutrients and bacteria, which the healthcare worker cannot see. Furthermore, this approach is unreliable as the healthcare worker may be distracted, or operating in an emergent environment with other priorities. The education approach does not solve the inherent weakness of the access device and places the health of the patient at the mercy of the unpredictable diligence of the potentially highly distracted healthcare worker.

One of the primary problems associated with access devices such as the luer valve is the failure of healthcare workers to scrub or otherwise prep the surface of the septum. At the least, healthcare workers would benefit from a reminder to scrub the surface before accessing the valve.

One embodiment of the present invention comprises a connection system comprising; a elastomeric septum defining an outer face, a cannula, which can be a male luer, having a distal end and defining at least one distal opening for flowing fluid out of the cannula, the opening defining at least one wall side wall facing the opening, the opening and the septum face being configured to minimize the contact of side wall with the septum face to minimize the potential transfer of microorganisms to the inner wall. The opening and the septum face can be configured such that the septum face does not engage the inner wall of the opening.

One embodiment of the present invention comprises a method for testing the cannula and septum system described above comprising; configuring at least one of a septum and a cannula such that the cannula can penetrate at least partially through the septum with reduced contact between the septum face and the opening, penetrating the septum with the cannula, testing at least one of the cannula and septum for the present of residual microorganisms which have passed at least partially through the septum during the penetration, modifying the configuration of at least one of a septum and a cannula to reduce the presence of residual microorganisms, and repeating at least steps a through c. An embodiment further comprises the step of adjusting the compression of the septum prior to the penetrating step. An embodiment further comprises the step of adjusting the durometer of the septum prior to the penetrating step. An embodiment further comprises the step of adjusting the composition of the septum prior to the penetrating step. An embodiment further comprises the step of adjusting the elastic modulus of the septum prior to the penetrating step. An embodiment further comprises the step of adjusting the composition of the septum prior to the penetrating step. An embodiment further comprises the step of adjusting the surface texture of the septum prior to the penetrating step. An embodiment further comprises the step of adjusting the shape of the face of the septum prior to the penetrating step. An embodiment further comprises the step of adjusting the shape of the opening of the cannula prior to the penetrating step. An embodiment further comprises the step of adjusting the angle of contact between the tip of the cannula or the opening prior to the penetrating step.

In another preferred embodiment of the swab pocket device. The swab pocket comprises a system or kit wherein a swab pocket and a swab are packaged in close association for example within a single common package and/or within connected sealed packages. Either or both the swab pocket and the swab may be wetted with one or more disinfectant solutions, which can for example be Isopropyl Alcohol (IPA), Chlorhexidine Gluconate (ChG), ethanol, and/or an iodaphor, to name a few, or any of a number of other liquid disinfectant solutions. The swab pocket and the swab could both be wetted with the same liquid disinfectant or they could be wetted with dissimilar liquid disinfectants. The liquid disinfectants could be dissimilar in a manner in which the swab has powerful and substantively instantaneous antimicrobial properties such as can be imparted by IPA, while the swab pocket has sustained and substantively long-term antimicrobial properties such as can be imparted by an IPA/ChG solution or in the alternative the IPA/ChG may be provided on the swab and the IPA only along the swab pocket.

This system or kit is suited for improved disinfection and cleansing of Luer Access Devices (LAD's) and for helping reduce and minimize bacterial contamination or bacterial load on the access surfaces of LAD's between uses. The system may be labeled in a manner in which the indication for use is to use the swab first then the swab pocket second. Indices would be provided on the package, preferably alphabetical or numeric, which distinguish the swabs two component parts, such as for example "Part 1", "Step 1" and/or "A" for the swab and "Part 2", "Step 2" and/or "B" for the swab pocket. This indication of order of sequential use provides users with a method for disinfection and protection according to the present invention.

One method of use is to, as "Step 1", open and remove the swab designated as "Part 1" and/or "A", from the package. Apply the disinfectant solution from the swab to the surfaces of the LAD being cleaned. Access the LAD and administer fluids or medicaments as required. Following injection, "Step 2" is performed wherein "Part 2" or "B" is opened and the swab pocket is removed. Apply the disinfectant solution from the outer surface of the swab pocket to the surfaces of the LAD previously accessed then advance the swab pocket over the LAD as previously described.

It can be appreciated that the first application of disinfectant solution from the swab is designed for primary disinfection of the access surfaces of the LAD to reduce the bacterial exposure during the subsequent access and injection of liquid into the LAD. Further, the subsequent application of disinfectant solution from the outer surface and/or at least one other surface of the swab pocket is designed to augment the primary disinfection and to minimize bacterial load on access surfaces of the LAD that may arise from the rebound of the piston, when the LAD is an open piston type luer access valve. In step two, the application of disinfectant solution and covering of the LAD via the swab pocket, post injection, is highly suitable for removing or killing bacteria which may have been displaced by the piston from the piston sidewalls, back into the area of the luer tip interface when the piston rebounds after an injection.

It is the purpose of the present invention to provide a system and method, which reminds the healthcare worker to clean the access device before accessing it.

It is the purpose of the present invention to provide a system and method, which provides a chemical agent which functions synergistically with a solid fluid wave to achieve mechanical elimination of bacteria during the insertion, retention, and/or withdrawal of an implement into and from an access device.

It is the purpose of the present invention to provide a system and method for developing medical devices, which achieve optimal mechanical elimination of bacteria during the insertion of an implement into an access device to reduce the dependence on the chemical elimination of bacteria.

It is the purpose of the present invention to provide a system and method which generates a comprehensive solid fluid wave to displace and/or destroy bacteria from the exposed portion of a medical implement which is inserted into an access device.

It is the purpose of the present invention to provide a system and method, which provides an outer face which is specifically shaped with internally projecting elastomeric walls (which can be a tube) to match the shape of the leading end of a tubular medical implement during insertion, such that a solid fluid wave derived of the elastomeric face is applied circumferentially to the leading end to eliminate bacteria from the leading end.

It is the purpose of the present invention to provide a system and method, which is designed to mechanically kill bacteria on medical access devices during the insertion of an implement into the access device using a highly flexible mechanical force, which overcomes both the flexibility and hiding defenses of bacteria.

It is the purpose of the present invention to provide a system and method, which is designed to kill bacteria carried by a medical implement by directed, forceful application of an elastomer against the implement during insertion of the implement into and/or through the access device.

It is the purpose of the present invention to provide a system and method, which is designed to specifically eliminate bacteria within an access device by combined chemical action and mechanical force against the bacterial cell wall.

It is the purpose of the present invention to provide a system and method, which is designed to provide an inexpensive valve cover which can provide this enhanced protection for a cost which does not greatly exceed the cost of the conventional prepackaged chlorhexidine disinfectant swab itself.

It is the purpose of the present invention to provide a system and method, which is designed to specifically kill bacteria within an access device by combined chemical action and mechanical compression to force the chemical agent into compressed juxtaposition with the cell walls of the bacteria to increase the exposure of the sacculus to the chemical agent.

It is the purpose of the present invention to provide a system and method, which is designed to specifically kill bacteria within an access device by combining a chemical agent with an elastomer and then by mechanically compressing the elastomer against a medical implement to increase at least the proximity and/or the release of the chemical agent to target bacteria on the implement.

It is the purpose of the present invention to provide a soft elastomer mounted within a rigid or elastic housing wherein the elastomer and housing are configured such that insertion of an implement against the elastomer causes enclosed compression of the elastomer by the housing to produce a predictable fluidic dispersion of the elastomer and thereby producing a solid fluid wave against the implement such that the bacteria residing on the implement and/or the elastomer are destroyed or displaced.

It is another purpose of the present invention to provide a soft elastomeric sated septum mounted within a rigid or elastic housing wherein the elastomer and housing are configured such that insertion of a male luer into the slit causes enclosed compression of the elastomer by the housing and against the male luer such that substantially all of the bacteria residing on the outside of the male luer are destroyed or wiped off.

It is the purpose of the present invention to provide a luer receiving septum with an upper face configured such that the outer edge of the circular end of the luer tip contacts the face first and deflects the face laterally so that the slit opens and the luer is advanced into the slit through the face with minimal or no forceful contact between the inner edge of circular end of the luer tip and the face to minimize the potential for the displacement of bacteria from the face to the inner edge of the luer.

It is the purpose of the present invention to provide a slitted luer receiving valve, which provides a tight resting compression force and which provides a release mechanism so that the compression force is releasable by an advancing male luer through the slit and wherein the force still provides a tight compression force against the wall of the advancing luer after the release so that the high compression force can tightly seal the resting slit and eliminate bacteria on the wall of the advancing luer so that the luer can be advanced through an area of tight resting compression with an insertion force which is less than would occur with a similar resting compression without the release mechanism.

It is the purpose of the present invention to provide a slitted elastomeric septum wherein the septum adjacent the slit is highly compressed by elastic supports (which supports can be elastomeric) which supports are at least partially collapsible releasing at least a portion of the compression over a short distance such that the high compression force is reestablished against the outer luer wall upon completion of the insertion of the luer into the slit.

It is further the purpose of the present invention to provide a luer-receiving valve, which also provides mitigation of negative pressure induced by withdrawal of the luer from the valve.

It is further the purpose of the present invention to provide a luer-receiving valve, which is capable of tight sealing about the luer for use with high-pressure injection.

It is further the purpose of the present invention to provide a luer-receiving valve or blunt cannula receiving system which a first slit (which can extend through the proximal face) with a long transverse axis extending along a first direction and a second slit (which can extend through the distal face) with a long transverse axis extending along a second direction, (which second direction can be perpendicular to the first direction) and wherein a first set of opposing slots can be provided aligned parallel to the first slit and a second set of opposing slots can be provided aligned parallel to the second slit.

BRIEF DESCRIPTION OF THE DRAWINGS

These, as well as other objects and advantages of this invention, will be more completely understood and appreciated by careful study of the following more detailed description of the presently preferred exemplary embodiments of the invention taken in conjunction with the accompanying drawings, in which:

FIG. 39a is a perspective view of a Swab Pocket with a slit for receiving a branch of a Y-site.

FIG. 39b is a longitudinal section view through another type of luer receiving valve covered by a Swab Pocket

FIG. 46 is a longitudinal section view of another embodiment of a luer receiving valve according to the present invention.

FIG. 47 is a front view of a two part Luer Access Device disinfecting system.

FIG. 48 is section view of a two part Luer Access Device disinfecting system showing a swab and swab pocket device respectively therein.

DESCRIPTION OF THE PRESENTLY PREFERRED EXEMPLARY EMBODIMENTS

Figure 6:
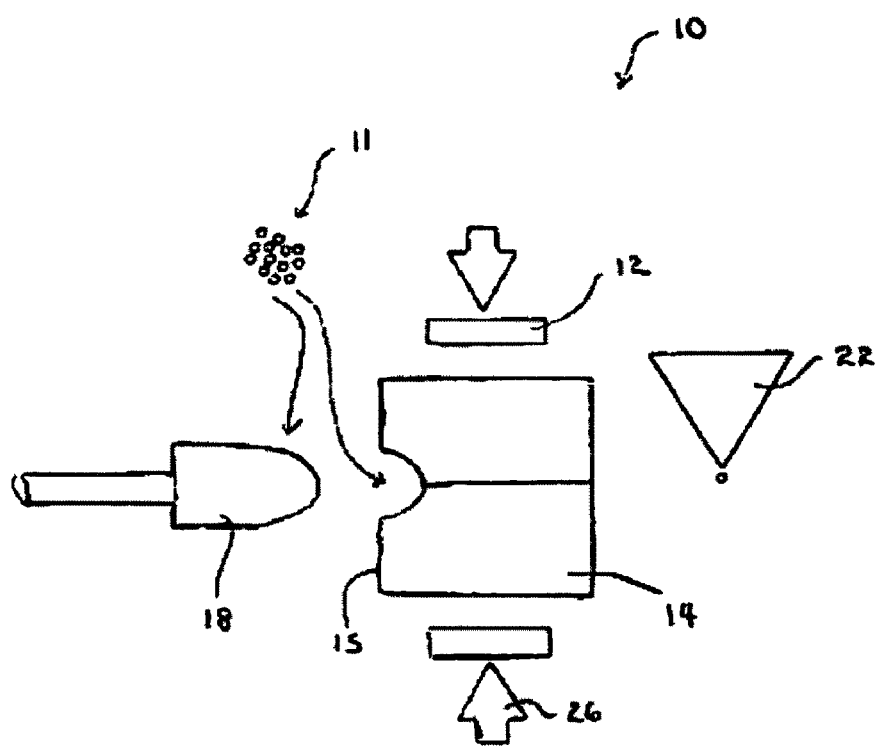
FIG. 6 is a schematic of a mechanical biocide testing system according to the present invention.

FIG. 6 shows a representation of the components of an embodiment of an elastomeric microorganism compression testing system 10 according to the present invention. The testing system 10 is designed for investigating the mechanical biocidal activity and solid fluid waves induced by various elastomers. The testing system 10 is also designed for developing mechanically biocidal devices, which achieve the optimal solid fluid wave for mechanical elimination of bacteria during the insertion and storage of an implement into the mechanically biocidal device.

The system 10 comprises a contamination source 11 (which can include bacteria or components and/or yeast colonies and/or a solution or an agent which simulates the behavior of the microorganism source), a compressing structure 12, and elastomer member 14 with an outer face 15, a compression receiving medical implement 18, and a biologic detector 22. The compressing structure 12 and/or elastomer member 14 can include a portion capable of providing adjustable compression (such as sloped walls or a frustum shape) or a compression adjuster 26 can be provided which delivers focused, and/or circumferential and/or comprehensive compression. The compressing structure may function to limit the displacement of the elastomer without resting compression. One purpose of the compressing structure is to provide for enclosed compression, which favors fluidic dispersion of the solid fluid wave in the opposite direction of the enclosure. The compression adjuster 26 can for example be configured to provide incremental adjustments as for example is provided by a rotating or otherwise progressively advancing compressing member 26. This can include comprehensive circumferential incremental compression and/or regionally focused compression as for example can be provided hose clamps of various lengths and cylindrical shapes. This example provides an illustrative example of an action, which can be provided by the compression adjuster 26.

Figure 7:
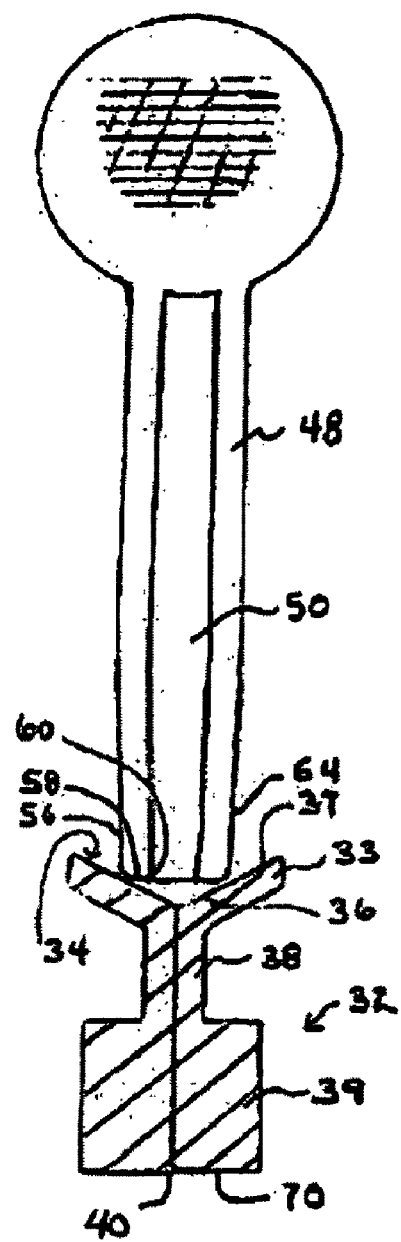
FIG. 7 is a schematic of a mechanical biocide testing system for a male luer according to the present invention.
Figure 8:
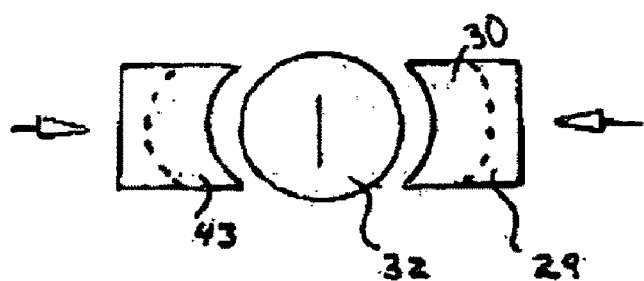
FIG. 8 is a schematic of the lower portion of the elastomeric receiver of figure with a schematic of a variable compressor of the mechanical biocide testing system of FIG. 7 according to the present invention.

FIGS. 7 & 8 shows a schematic of an embodiment of the components of an elastomeric microorganism compression testing system 27 with a separate suspension of bacteria 28, a rigid compressing structure comprised of a rigid outer housing schematically shown as 29 (FIG. 8) having an upper surface 30 angled radially upwardly configured to provide enclosed compression of an internal elastomeric septum 32 with an upper portion 33 having an outer face 34. The housing can have a configuration similar to that of FIG. 11 but with portions removed and replaced with adjustable compressing windows. The outer face 34 includes a central face portion 36 and a peripheral face portion 37, the septum 32 provides an extension portion 38 and a lower portion 39 and a central slit 40 extending from the face 34 through the extension portion 38 and lower portion 39. Slots 43 below the surface 30 are provided between the septum 33 and housing 29.

The basic configuration can be for example, similar to the device shown in U.S. Pat. No. 6,171,287, of the present inventor but with the lower female luer connector removed and an opening provided for projection of an elongated medical implement which as shown is an elongated male luer simulator 48 having an internal lumen 50 and a distal tip 56 with a circular distal end 58. The distal tip 56 defines internal wall portion 60 adjacent the end 58 and further defines an external wall 64. In operation, the suspension of bacteria 11 are applied to the face 35 and/or at least a portion of external wall 56 of the male luer simulator 48. A selected portion of the male luer simulator 48 or a portion of the face 35 may be contaminated with the suspension 11. The suspension 11 can be allowed to dry if desired and/or an antiseptic may be applied to the face 34 to simulate conventional practice of wiping the septum. The male luer simulator 48 is then advanced through the slit at the face 34 and through the extension portion 38 and the lower portion 39 to project beyond the lower portion 39. A biologic detector (or a biologic testing system or method) can then be applied to determine the location, extent, and or number of bacteria contaminating of the tip 64 of the male luer simulator 48 projecting through the lower face 70. Since the bacteria are killed or wiped off by mechanical force which is in part dependent on the advancing force, the advancing force (and/or speed) of advancement the male luer simulator 48 can be controlled and/or varied if desired by using a mechanical advancing device (not shown) to simulate the ranges of advancing forces which may be applied in clinical practice. A video microscope may be used to investigate the behavior of the solid fluid wave and its relationship to the male luer simulator 48. In addition a pressure transducer (not shown) can be embedded in the sidewall or at the end of the luer simulator 48 to measure the compressing force of the elastomer. If desired multiple transducers may be positioned and a pressure force curve generated for each of the different regions of the male luer simulator over the period of advancement and at the end of advancement (and for the withdrawal period if desired).

Once the initial testing has been completed the housing dimensions and/or shape and/or the elastomer dimensions and/or shape, and the durometer, elastic modulus, surface coating, and molecular structure, lubrication, and components of the elastomer can be adjusted to vary the compression, adhesive forces, and shear forces at various regions of the male luer simulator during advancement to enhance the mechanical elimination of the microorganisms. After adjustment, the male luer simulator 48 can be re-advanced and the biologic residual after advancement retested. For example after an initial trial, the septum 32 can be molded with the upper portion 33 thickened by, for example 0.5-2 mm or the angle or shape of the face 34 changed, the upper portion of the housing 31 may be molded in a more upward ramping configuration, a hydrophilic or antimicrobial coating, and/or a coating or process which microscopically roughens the surface to increase the shear force on bacteria may be added, material such as thin vanes (not shown) may be added to the slots 43, the extension portion 38 or housing wall adjacent the extension portion 38 may be thickened (for example by 0.1 mm), the lower portion 32 may be thickened or placed into a configuration of focused compression on the slit 40. Each process can be incremented and repeated until the optimal configuration is identified.

Figure 9:
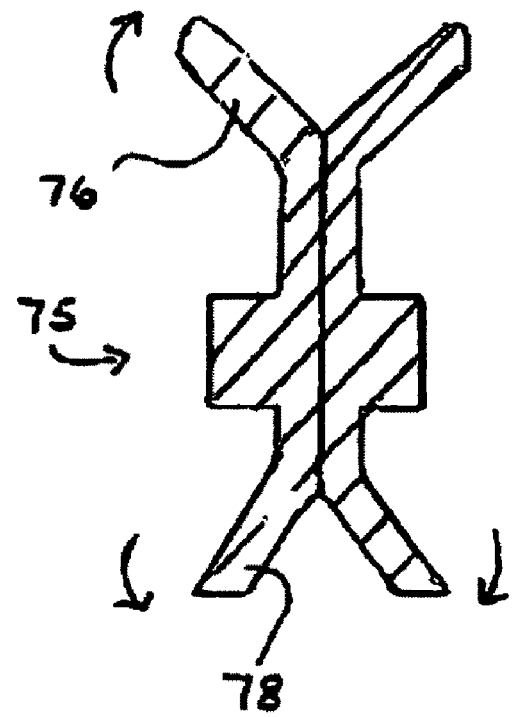
FIG. 9 is a schematic of an alternative elastomeric receiver of a mechanical biocide testing system of FIG. 7 according to the present invention.
Figure 10:
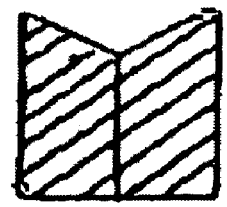
FIG. 10 is a schematic of an alternative elastomeric receiver of a mechanical biocide testing system of FIG. 7 according to the present invention.

FIGS. 9 and 10 show simple alternative elastomeric septums for receiving the simulator 48 and for testing different configurations. The septum 75 of FIG. 9 includes an adjustable upper portion 76 and an adjustable lower portion 78. These can be fixed in each progressive position by molded housings of various dimensions or by a rigid or elastic adjustable support (not shown).

Figure 11:
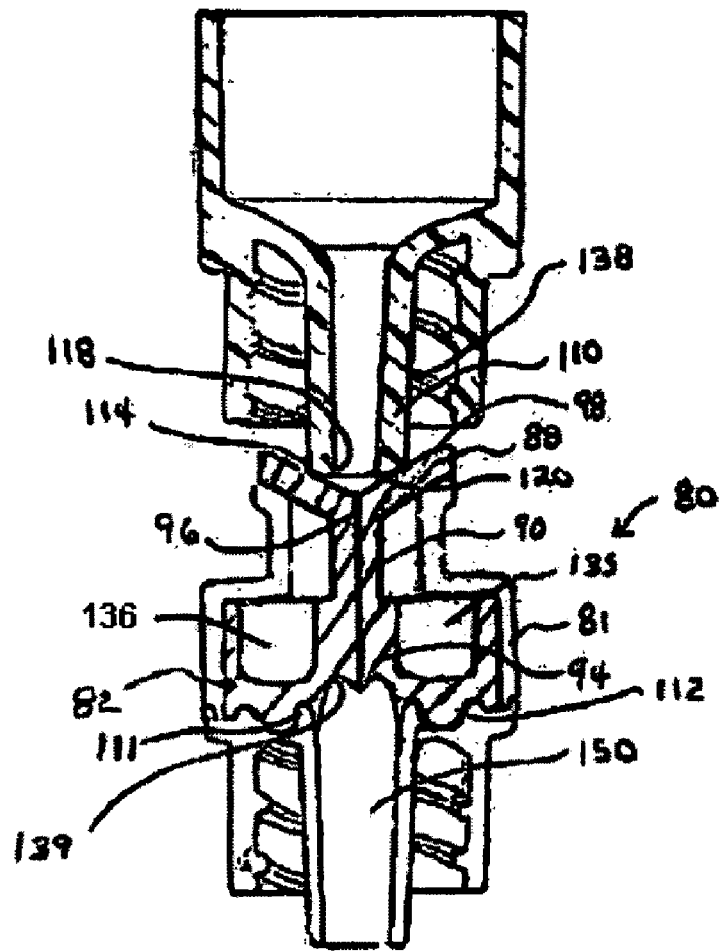
FIG. 11 is a central section view cut perpendicular to the slit of an embodiment of a luer receiving valve configured to destroy and/or displace microorganisms on the penetrating portion of a luer lock or luer slip connector.
Figure 12:
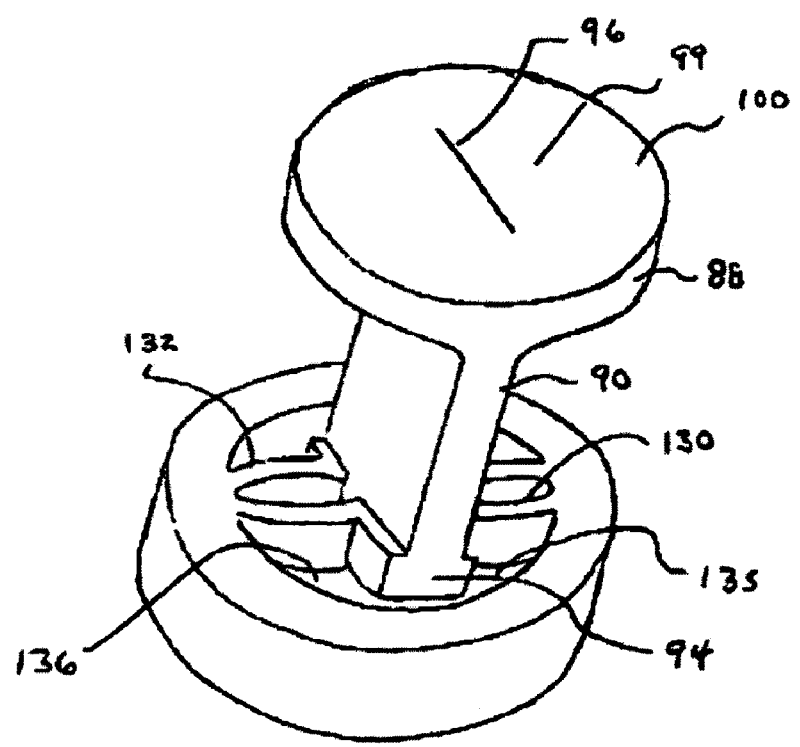
FIG. 12 is a perspective view of an embodiment of the septum for use with the housing of FIG. 11.
Figure 13:
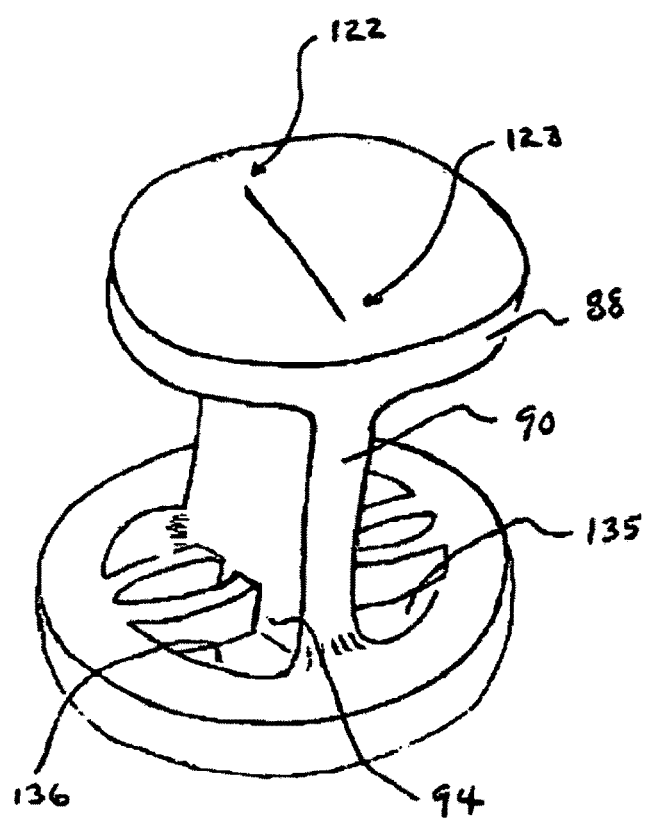
FIG. 13 is a perspective view of an alternative embodiment of the septum for use with the housing of FIG. 11.

FIGS. 11-18 show various configurations of a luer-receiving valve 80 configured to have specific regions for adjustment of compression forces to allow ready optimization as a mechanical biocide. The valve 80 includes an outer housing 81 and an elastomeric septum 82 mounted with the housing 81. The septum 82 includes an upper portion 88 an extension 90 and a lower portion 94 and a central slit 96. The upper portion 88 includes an outer face 98 having a facial central portion 99 and a facial peripheral portion 100 (FIG. 12). The face 98 is configured to receive a male luer 110. The upper portion 88 is sloped upwardly at an angle such that the outer edge 114 of the distal end 120 of the male luer 110 engages the outer face 98 and deflects the slit 96 open so that the inner edge 118 of the distal end 120 of male luer 110 does not forcefully engage the outer face 98 but rather passes into the slit 96 as the outer face 98 deflects laterally. When mounted with the housing 81, the facial peripheral portion 100 (FIG. 12) of the upper portion 88 is deflected upwardly to provided focused compression adjacent the upper surface of slit 96 and this an adjustable angle which allows ready optimization of both the compression force at the slit 96, the angle of engagement of the distal end 120 of the male luer 110 and the compression and/or shear force of the septum 82 against the luer 110 during penetration. In one embodiment the angle is about 30-45 degrees but other angles may be used. Because the slit begins to open early, the slit begins to shorten early placing compression on the advancing distal end 120 even at the ends 122 and 123 of the slit 96 (FIG. 13). If desired the slit 96 can be shortened to a length less than the outer diameter of the luer 110 to increase the compression on the external wall 64 at the ends 122 and 123 of the slit 96. If desired the slit can be less than 75% of the outer diameter of the luer or can comprise a triangular shaped slit which extends distally as a simple perforation below the apex of the triangle.

Figure 14:
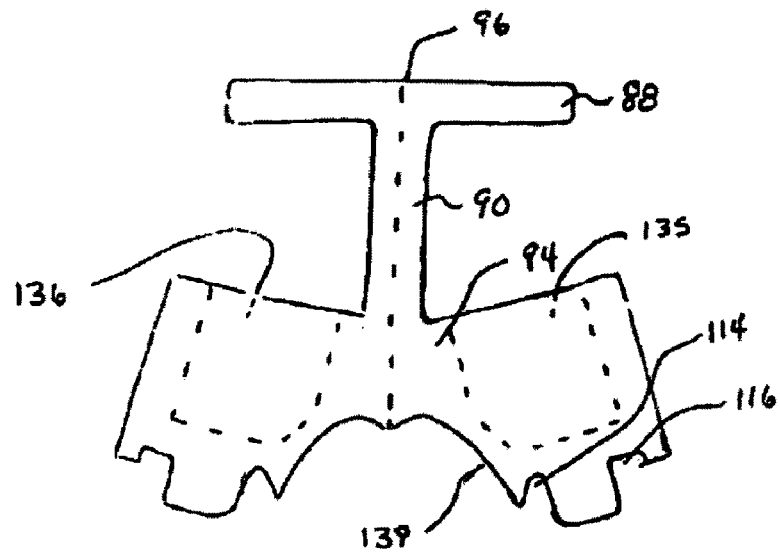
FIG. 14 is a side view of an embodiment of the septum of FIG. 12 showing the resting configuration before installation into the housing.
Figure 14A:
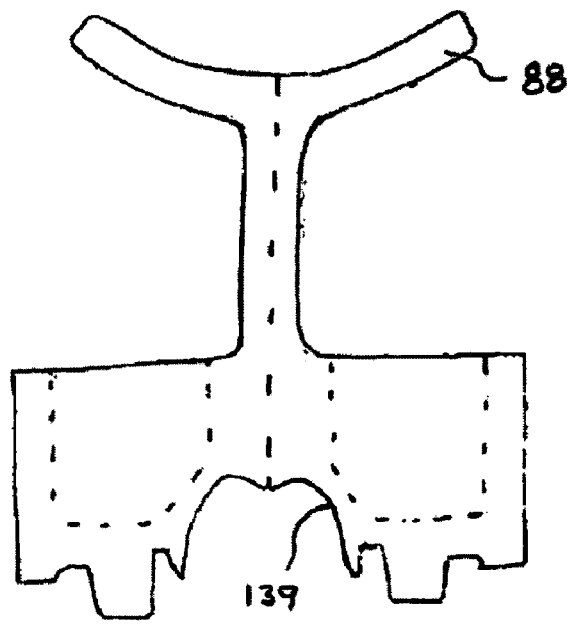
FIG. 14a is a side view of an embodiment of the septum of FIG. 12 showing the compressed configuration after installation into the housing.
Figure 15:
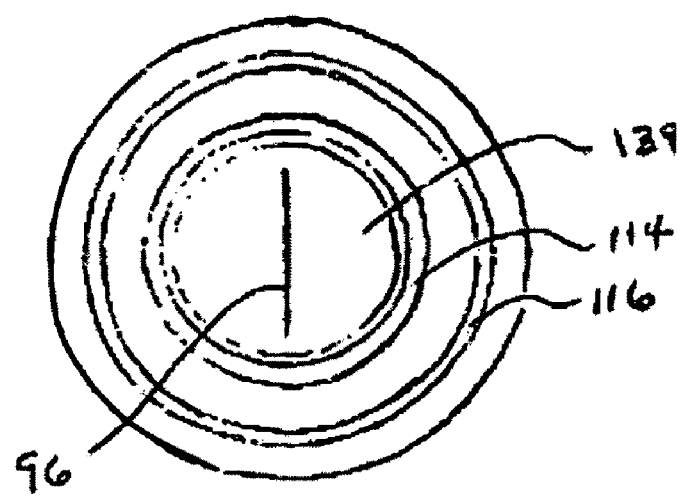
FIG. 15 is a bottom view of the lower portion of an alternative embodiment of the septum of FIG. 12.
Figure 16:
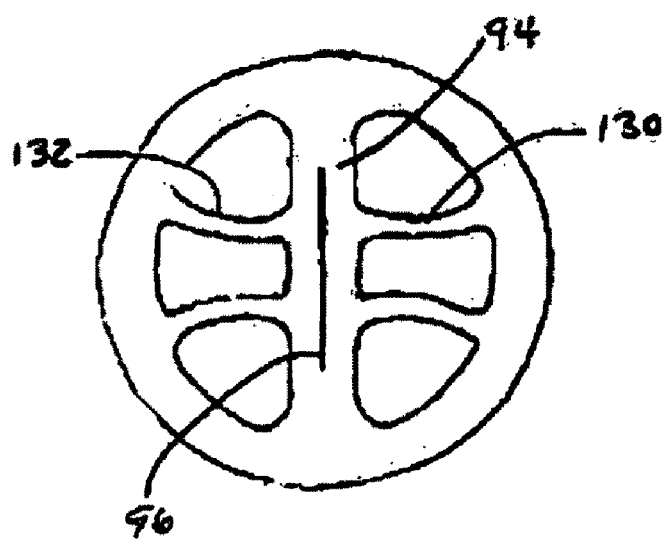
FIG. 16 is a transverse section view of the lower portion of an alternative embodiment of the septum for use with the housing of FIG. 11.
Figure 17:
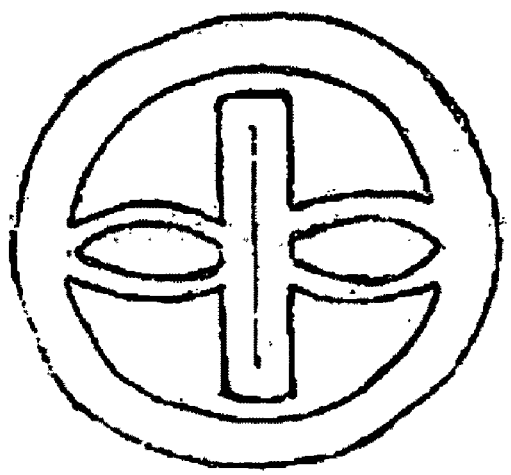
FIG. 17 is a transverse section view of the lower portion of an alternative embodiment of the septum for use with the housing of FIG. 11.
Figure 18:
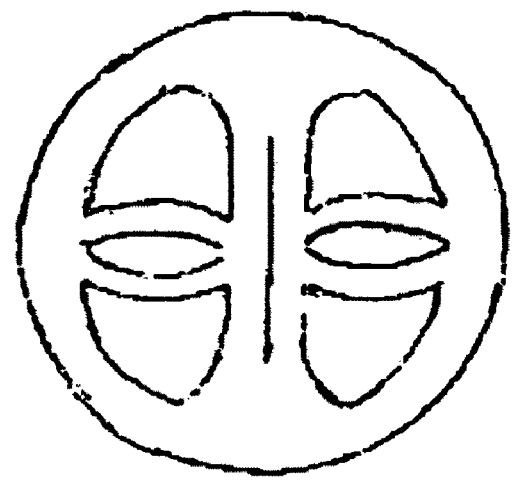
FIG. 18 is a transverse section view of the lower portion of an alternative embodiment of the septum for use with the housing of FIG. 11.

The lower portion 94 is seated on annular projections, 111 and 112 which seat within recesses 114 and 116 (FIG. 15). The lower portion 94 is supported by opposing pairs of compression inducers comprising elastic support columns 130 & 132 (FIG. 12) directed toward the slit 94 and bowed outwardly to facilitate collapse on compression induced by the luer through the column as will be described. The columns define slots 135 and 136 for receiving the displaced lower portion 94 and for receiving the outwardly collapsed columns 130 & 132 during luer penetration. As shown in FIG. 14, the lower portion 94 can be molded with an upward angle and this can be an adjustable molded angle, which allows ready optimization of both the compression force at the slit, the compression and shear force of the septum 82 against the outer wall 138 of the luer 110 during penetration without changing the housing configuration. In one embodiment the angle of the lower portion 94 as molded is about 20-45 degrees but other angles may be used. This also has the favorable effect of exerting an upward focused compression force to resting slit 96 at the lower face 139 of the septum 82. During downward deflection of the lower portion 94 during assembly, the columns 130 & 132 would be defected internally into a more parallel configuration but the outer housing 81 compresses the columns 130 & 132 toward the slit such that the columns 130 & 132 again bow outwardly to near the collapsing position thereby setting the slit 96 in a highly compressed position which is releasable by advancement of the luer. The advancing luer induces the release by collapsing the columns 130 & 132.

One advantage of this configuration is achieved by the longitudinal mass of the columns, which will tend to carry lateral movement of the septum downward. When the advancing luer 110 collapses the columns 130 &132, the elastic laterally directed force of the collapse is carried longitudinally along the distal aspect of the slit 96 and this enlarges the size of the distal opening of the slit 96 beyond distal end 120 of the luer 110 to open the slit 96. This column deflection below the distal end of the luer 110 enhances the elastomeric space below the fully advanced luer 110. In one embodiment the distal end 120 of luer 110 fails to reach the end of slit 96 when maximally advanced so that the distal opening of the slit 96 beyond distal end 120 of the luer 110 is reliably present. (The formation of an elastomeric flow space within as septum below the fully advanced luer is discussed in U.S. Pat. No. 6,171,287 of the present inventor). The space is enlarged when the luer 110 is fully advanced and rebounds to reduce in size when the luer 110 is retracted thereby mitigating or eliminating any negative pressure deflection in the channel 150 below the lower face 139 of the septum 82 or inducing positive pressure in that channel 150. The flow channel 150 below the lower face 139 is configured such that it is easily flushed by fluid from the luer and this is facilitated by positioning the maximum advancement of the distal end 120 of the male luer 110 above the lower face 139. If desired a flow deflector (not shown) to induce turbulent flow within the flow channel can be provided. Also, if desired, the slot 135 and/or the slot 136 can be connected downward to the open space within the lower luer lock connector (adjacent the male luer projecting within the luer lock connector and about the fluid channel 150) within the male luer by fenestrations of other connections through the septum 82.

Figure 19:
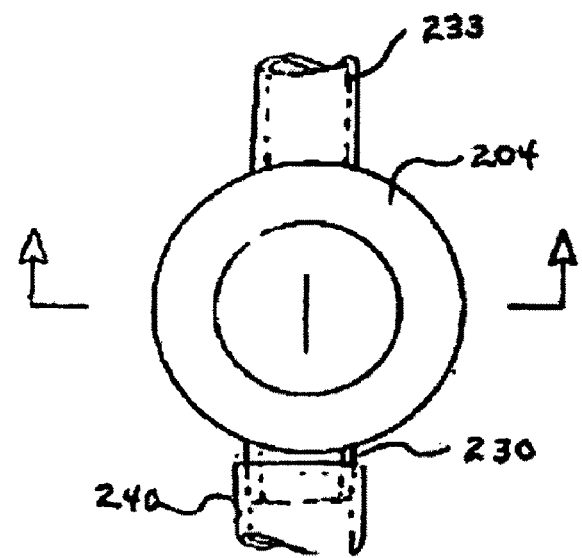
FIG. 19 is a top view of a dead space free valve similar to the valve of FIG. 11 especially useful for blood sampling.
Figure 20:
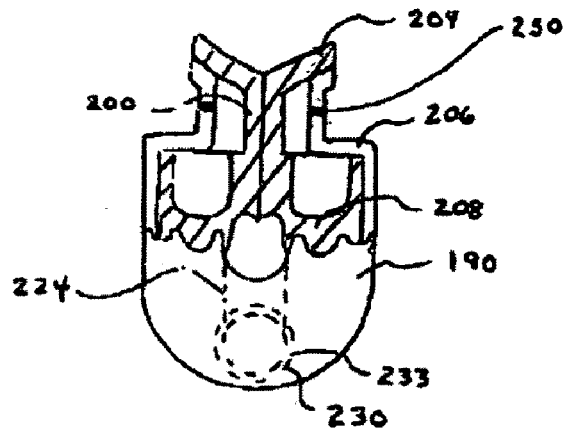
FIG. 20 is a section view of the dead space free valve of FIG. 19.

FIGS. 19 and 20 show a luer-receiving valve similar to the valve of FIG. 11 but with a lower housing 190 modified to provide a dead space free configuration. The septum 200 includes an upper portion 204 mounted above housing 206 and a lower portion 208 sealed against lower housing portion 190. Ramped flow channel 224 extends from an inlet 230 to a position below the septum lower portion 208 and through an outlet 233. Flexible medical tubing is shown attached to the inlet 240. This type of design is particularly suitable for blood collection and for blood tubing, as is used in dialysis or arterial lines. An indicator 250 which can be circumferential, visual, or tactile and positioned for example at the point so that the luer tip is within the extension and the lower slit is closed when the luer lock housing first exposes the visual indicator. The nurse can be instructed to withdraw blood into a syringe with a luer lock connector (of the type shown in FIG. 11) attached to the valve, then to rotate the luer lock connector slowly off the valve until the indicator is visible below the luer lock connector. At this point the nurse lightly retracts the syringe piston to decompress the syringe and then remove the syringe from the valve. The indicator indicates a position wherein the septum lower portion occludes the luer tip so that the interior of the syringe can be decompressed.

Figure 21:
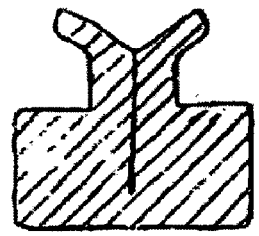
FIG. 21 is a section view of a luer receiving mechanical biocidal cap or docking station constructed entirely out of elastomer

FIG. 21 shows an elastomeric luer-receiving cap or docking station, which is configured to protect the luer during storage. This cap can be, at least partially, comprised of an elastomer of a higher durometer. The upper portion of the cap is designed to fill the luer lock connector.

Figure 22:
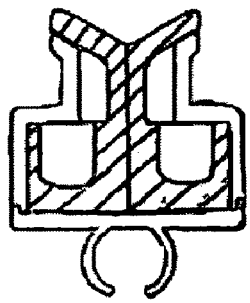
FIG. 22 is a section view of a luer receiving mechanical biocidal cap or docking station with an internal elastomer and an outer rigid housing.

FIG. 22 shows a cap configured in a manner similar to the valve of FIG. 11 but with a dead end and a connector for connection to tubing or other structure.

Figure 23:
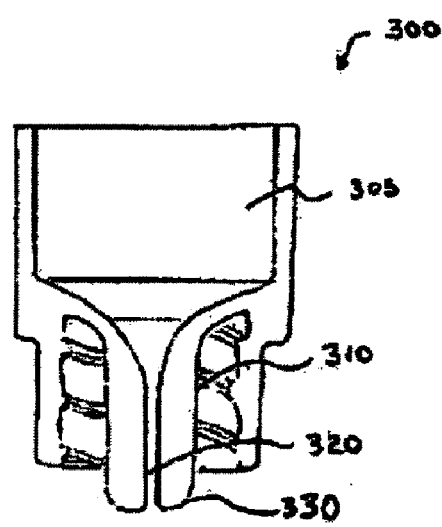
FIG. 23 is a section view of a modified male luer.

FIG. 23 shows a pre-filled single use catheter flush syringe for flushing IV catheters. The syringe is conventional except that the male luer is modified to produce a reduced exposure of the lumen at the distal tip of the male luer and thereby increase the mechanical biocidal effect of the luer valve of FIG. 11. The syringe 300 has a large diameter bore (as is used with the Posiflush Syringe, for example marketed by Becton Dickinson). The male luer 310 of the syringe includes a very narrow internal lumen 320 (such as a lumen diameter of 1 mm or less) and tapered outer sides 330 of the distal end of the male luer 310. The large lumen is not necessary for flush maneuvers and reduces the contamination exposure area of the lumen at the tip of the male luer. The smaller lumen also can increase the turbulence immediately below the tip of the syringe, which may have a favorable effect in the flushing of certain valves. However the proximal restriction to flow can reduce the velocity of the jet which projects distally at the end of the catheter, which may have a favorable effect on delicate endothelium of the vein especially for short peripheral catheters in small veins. However this restriction to flow can be reduced by limiting the length of the narrowing if desired. According to an embodiment of the present invention a medical implement (such as a male luer) is configured to match the configuration of the elastomer to optimize the mechanical anti-infectivity of the combined implement/elastomer system during operation. In an example, a filled catheter flush syringe with a luer having a large bore diameter and a tip shaped to provide limited exposure of the lumen and a small distal internal lumen is provided to reduce the potential for contamination of the internal lumen of the luer, to facilitate flushing of the access devices, and to reduce the velocity of the flow jet against the endothelium wall. Although the anti infective characteristics of the valves in FIGS. 11 and 20 reduce or eliminate the need for external protection, if desired the protective caps of FIG. 21 and/or FIG. 22 can be configured to receive and cap a luer valve itself (such as a those shown in FIG. 11 or 20) compressing the face of the valve against a protective and mechanically and/or chemically active biocide.

Alternatively a protector for luer valves (such as the valve of FIGS. 11 and 20) can comprise an antiseptic containing fabric or gel on one side bonded or otherwise secure attached on the other side with an elastomer or flexible polymer, which can be moldable during use. The protector can be configured in a swab pocketor planar configuration and covered by an outer envelope of the type used for example with 70% alcohol swabs.

Figure 25:
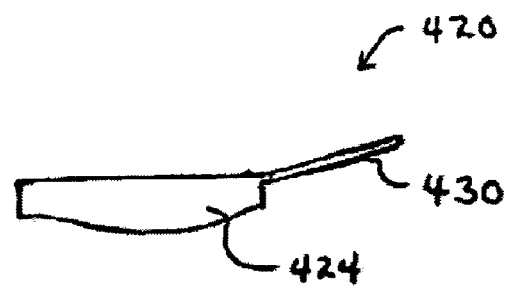
FIG. 25 is a side view of a disposable anti infective cap insert.
Figure 26:
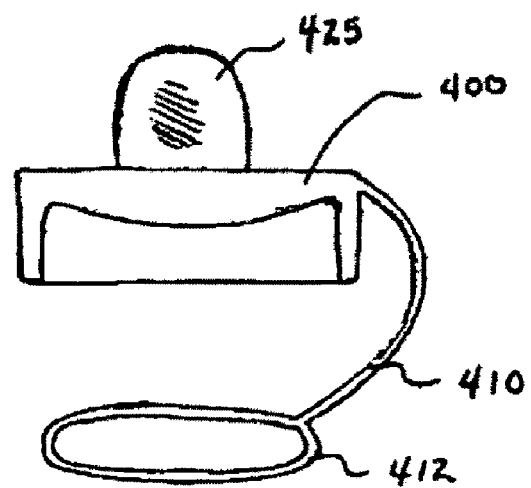
FIG. 26 is a side view of an elastic flip cap for protecting luer valves or septums.

In one embodiment a rotate able flip cap 400 is provided connected with the valve by a living plastic hinge or short flexible filament 410 with a circular loop 412 for connection about the valve, the flip cap 400 is designed to receive a replaceable anti infective insert 420 (FIGS. 24-26), which can be a small fabric swab containing an anti-infective agent for mounting within the cap 400 or over the valve. The flip cap 400 can be flexible and elastic so as to enlarge in size for insertion over the valve and insert 420 so that the friction fit is secure without rotation or a locking mechanism. The flip cap 400 can contain or be comprised of an elastomer, which presses the intervening insert 420 against the valve face when the cap 400 is applied. In an embodiment shown in FIG. 24 the insert 420 may be packaged in a watertight tear able container 422 has a circular portion 424 and a handle 430 (which can be non-absorbent), which extends away from the swab the handle extends out from under the cap 400 when the cap 400 is applied over the insert 420 against the valve face. When the nurse desires to access the valve, the cap 400 with the contained circular portion 424 is rotated, as by rotating projection 425, with pressure thereby rubbing the circular portion 424 against the valve face and then the cap 400 is pulled off the valve. The valve is then accessed. The handle 430 is grasped to pull the circular portion out of the cap 400. A new insert 420 is then applied with the cap and the cap 400 is flipped closed. In another embodiment (not shown) the insert is a swab pocket of fabric or other absorbent material placed over the valve, and then the cap 400 is flipped to snap over the fabric and the underlying valve. The cap 400 can be flexible and elastic so as to enlarge in size for insertion over the valve and insert or fabric swab pocket so that the friction fit is secure without rotation or a locking mechanism although a thread or other locking mechanism may be provided.

In one embodiment (not shown) the cap also includes a projecting member which is sized to be received into the slit. This member can for example be impregnated with an anti infective agent or can contain an anti infective agent which is released when the member is compressed by the slit wall of the valve.

It should be understood that many valve configurations are included within this teaching. The face could comprise a funnel shape or a partial funnel shape. The upper portion can vary in thickness from the central to the peripheral position. The thickness of the columns could vary between the more proximal column portions and the distal column portions. The elastomer could be iodinated or contain pockets containing an anti-infective agent or an agent, which alters the elastic modulus of the sacculus. The biocidal and bio-displacement action of the elastomeric solid fluid wave can be applied to other medical devices. For example, smooth planar areas, which need frequent clearing of bacteria such as a food preparation surface, can be engaged by elastomeric compression as, for example, by an elongated solid fluid wave. The force of the pressured application of the elastomer against a surface, the frequency of application and the scope of the advance of the solid fluid wave can be automated. To enhance the sliding action of the solid fluid wave the elastomer can be highly compressed over only a very thin region such as 1-4 mm. This approach may be particularly useful for use to produce mechanically biocidal syringe barrel and piston configurations where resistance to advancement is a very important feature.

Figure 27:
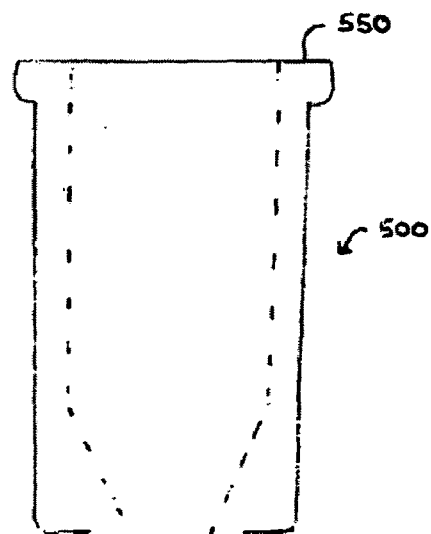
FIG. 27 is a side view of a blunt cannula configured to minimize outer mechanically protected zones for bacteria.
Figure 27A:
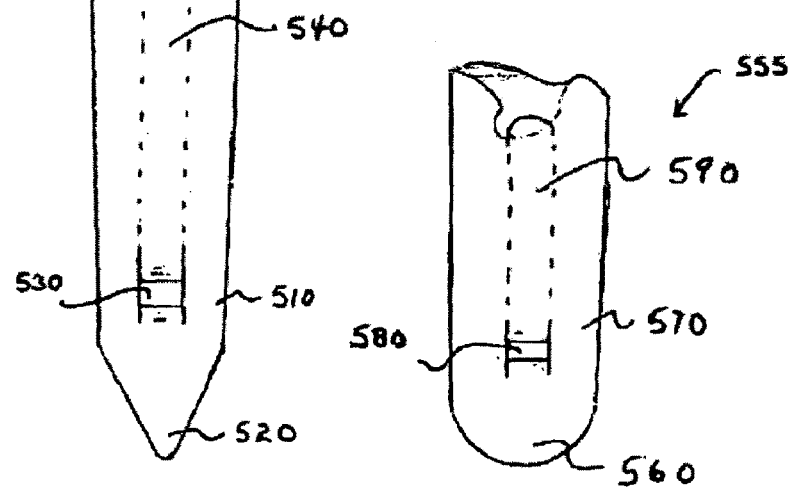
FIG. 27a is a broken side view of a blunt cannula configured to minimize outer mechanically protected zones for bacteria.
Figure 28:
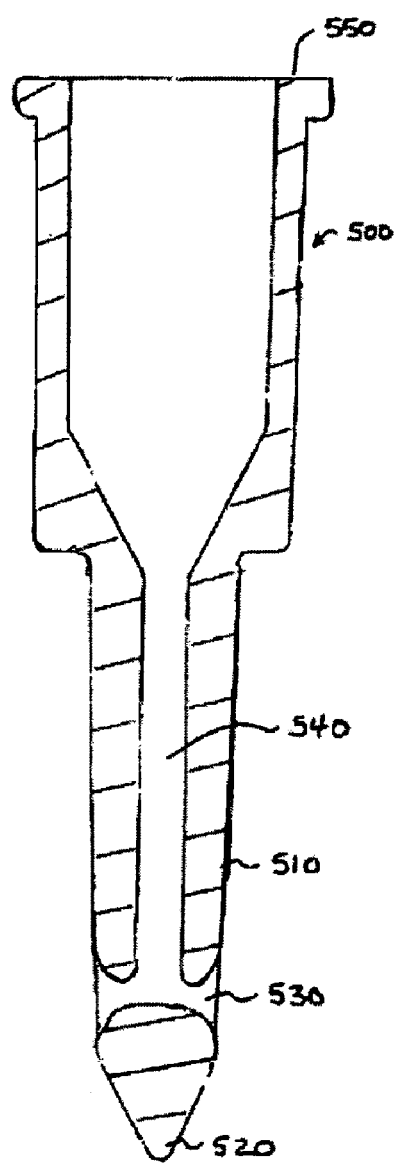
FIG. 28 is a section view of a blunt cannula of FIG. 27.
Figure 29:
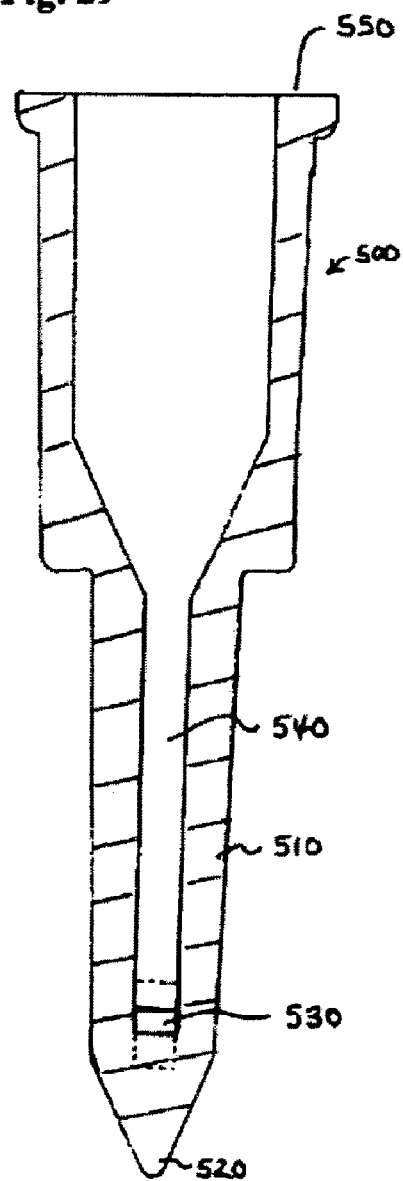
FIG. 29 is a section view of a blunt cannula of FIG. 27.

In another embodiment as shown in FIG. 27-29, a mechanically biocidal blunt cannula 500 is provided which is specifically configured to optimize comprehensive mechanical force against the outer wall 510 of the cannula and to reduce the potential for bacteria adjacent the distal opening to escape the wiping or compressive mechanical force of the septum during insertion and withdrawal into and from an elastomeric septum. The cannula 500 has a solid distal tip 520 which can be sharp or blunt and at least one distal opening 530 adjacent the tip which extends to a lumen 540 within the cannula. The cannula has a proximal end 550 for connection with a luer. The distal opening 530 slopes interiorly so that bacteria carried along by the solid fluid wave are not deposited on an edge adjacent the opening but rather carried past the opening or otherwise destroyed during the insertion process. FIG. 27*a* shows an alternative biocidal cannula 555 configuration with a solid distal tip 560 and outer wall 570 a distal opening 580 and a lumen 590.

Figure 30:
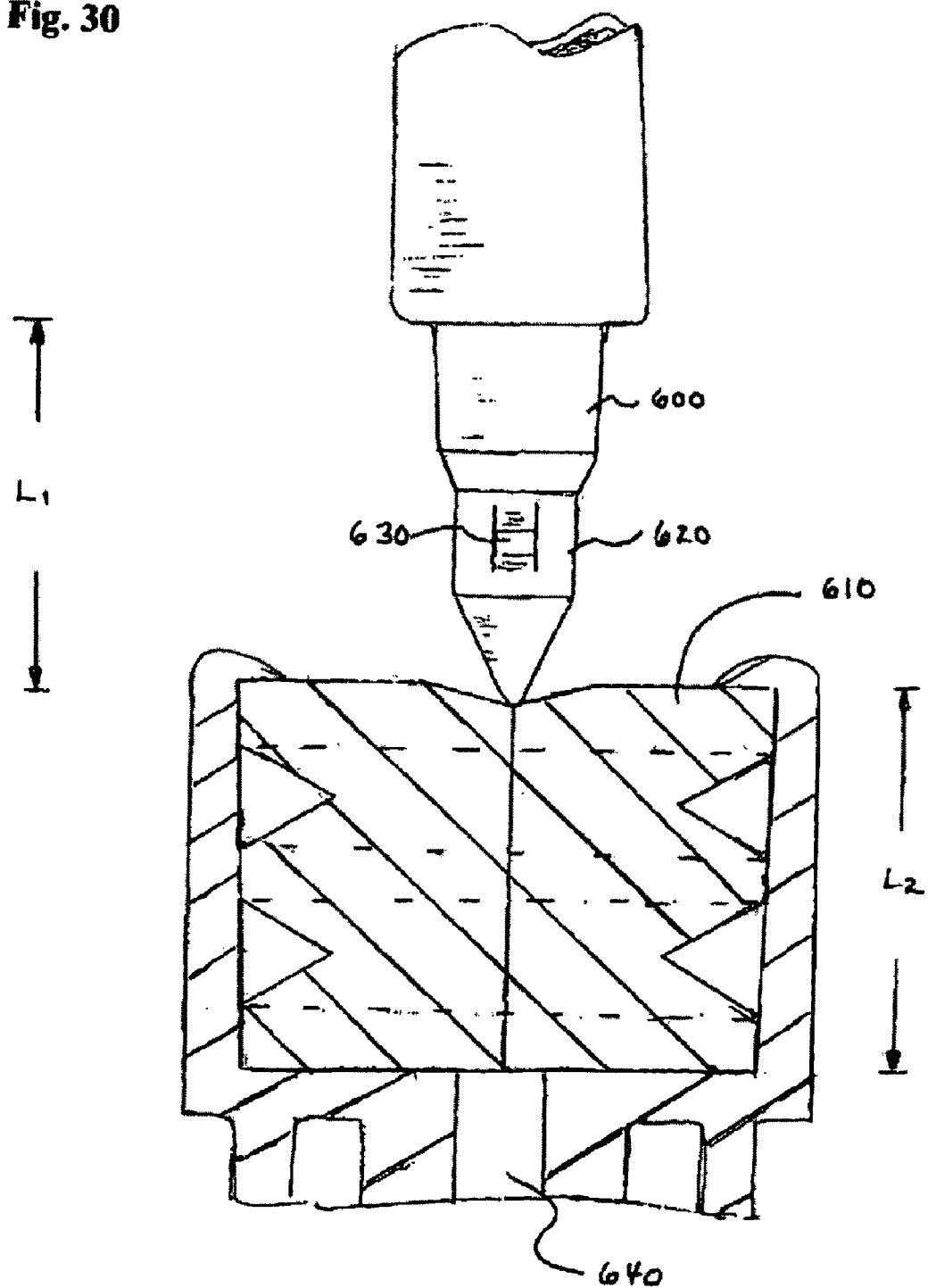
FIG. 30 is a side view of a blunt cannula with rapidly varying sidewall dimensions.

FIG. 30 shows an alternative embodiment of a mechanically biocidal cannula 600 with a variable outer dimension for insertion into a septum 610. The cannula has a distal portion 620 with a lesser diameter adjacent the opening 630 and a larger diameter portion 640 adjacent the opening 630. The larger upper dimension holds the slit apart to a greater extent than the diameter of the distal portion 620 to allow fluid to flow from the opening 630 and into the flow path 640 below the septum 610 when the L2 is of greater length than L1. This eliminates negative pressure within the flow path 640 associated with withdrawal of the biocidal cannula 600. If preferred the septum 610 can be as long, longer, or nearly as long as the cannula 600 and is preferably under compression (which may be variable) thereby increasing the compressive contact with the cannula 600.

In an embodiment a method of monitoring an IV system for contamination is provided, the method comprises steps of advancing a male luer into a valve and investigating the male luer outer portion, such as the tip, for evidence of contamination subsequent to the advancing step. In one embodiment the male luer functions as a probe (or a swab), which enters the valve in question and collects a specimen (as on its outer surface) from the interior of the valve for assessment. The evaluation of the male luer (such as the outer surface of the male luer) may be a routine part of IV access. The biologic detector may be mounted on the IV pole and used to access the luer before and/or after each connection or can be employed for spot surveillance purposes. In an alternative embodiment, used for surveillance, a specialized swab or collection device fashioned in the shape of a male luer may be provided.

Figure 31:
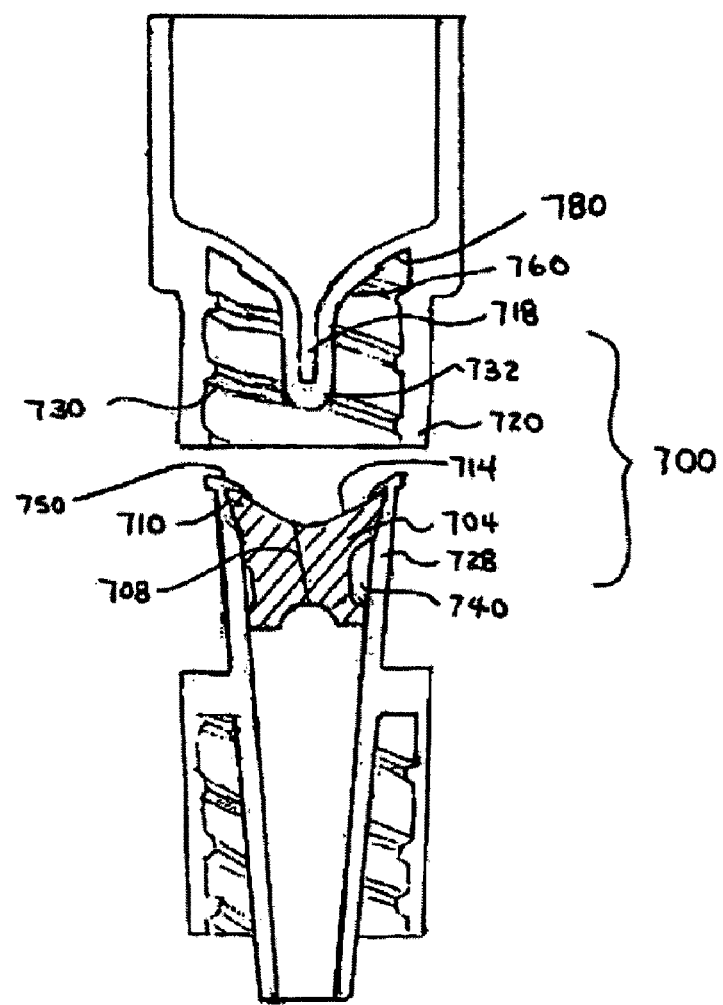
FIG. 31 is a longitudinal section view of a mechanical biocidal cannula and septum system.

FIG. 31 shows a combination mechanically biocidal cannula and septum system 700 wherein the septum 704 has a central slit or perforation 708 and the septum 704 is under high compression. The septum 704 can be cylindrical and wedged into a frustum shaped receiver to provide greater compression from its proximal to distal extent to allow easy penetration with but high distal compression force. The upper portion 710 can be displaced proximally to increase the compression at the upper surface 714. In one embodiment the septum 704 is of a durometer of about 10-30 or less so that the elastomer flows under high compression will enter microscopic crevices wherein bacteria may otherwise be protected from compression or shear forces. The cannula 718 can have a centering member 720 such as a longitudinal guide, which engages a distal end, 724 of the septum housing 728. If preferred a very short slit (or only a preperforation induced by a needle) and/or compression force can be high during the insertion which can result in penetration forces which are high. According to one aspect of the invention an advancing (penetration) force amplifier (such as projecting threads 730) is provided and engaged prior to the contact of the tip 732 of the cannula 718 to the compressed septum so that the nurse does not perceive the penetration forces as high and rather has a ready mechanism to overcome the penetration force by simply aligning the centering member 720 of the cannula 718 and the septum housing 728 and then threading the centering member 720 onto the housing 728.

Figure 31A:
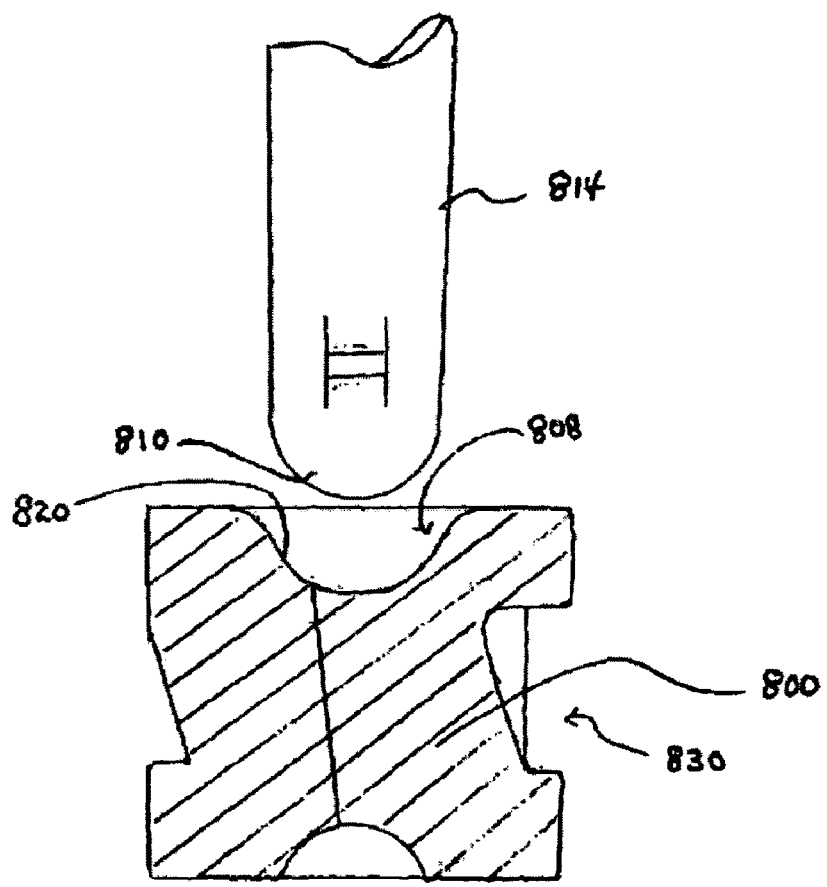
FIG. 31a is a broken longitudinal section view of a mechanical biocidal cannula and septum system.
Figure 32:
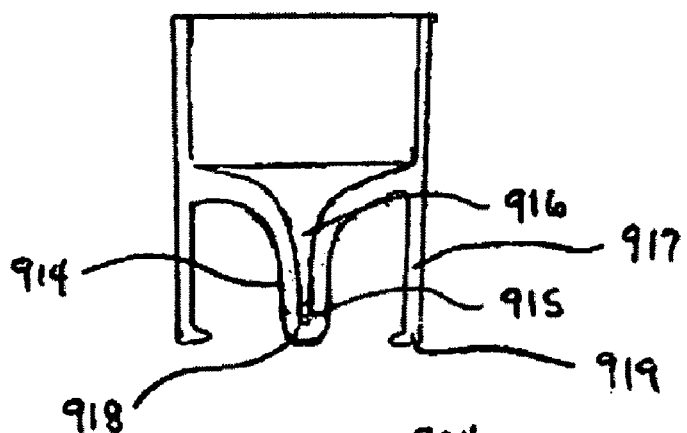
FIG. 32 is a longitudinal section view of a mechanical biocidal cannula.
Figure 33:
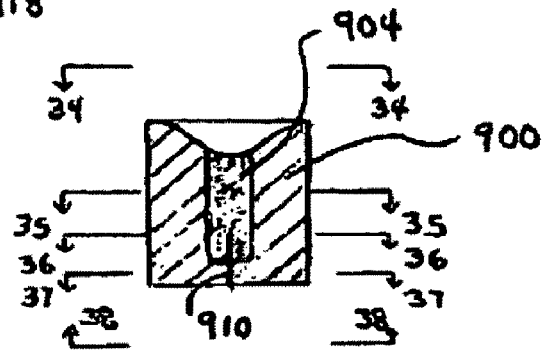
FIG. 33 is a longitudinal section view of a mechanical biocidal septum.
Figure 34:
FIG. 34 is a top view the mechanical biocidal septum of FIG. 33.
Figure 35:
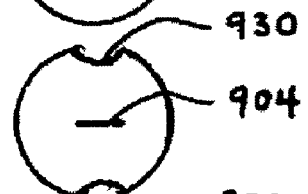
FIG. 35 is a transverse section view through 35-35 of FIG. 33 showing the proximal slit orientation and the slots aligned with the proximal slit.
Figure 36:
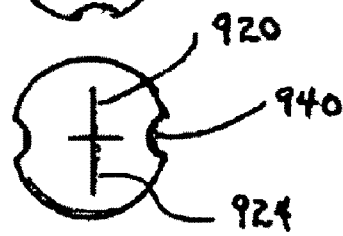
FIG. 36 is a transverse section view through 36-36 of FIG. 33 showing the proximal slit and distal slit orientation and slots aligned with the distal slit.
Figure 37:
FIG. 37 is a transverse section view through 37-37 of FIG. 33 showing the distal slit orientation.
Figure 38:
FIG. 38 is a bottom view of the septum of FIG. 33.

As shown in FIG. 31 (and also in FIG. 31*a*) the slit or perforation 708 (FIG. 31) can be offset from the center to reduce the potential for the development of a reduced zone of compression at the distal tip 732 of the cannula 718. A larger receptacle or slot 740 may be present on the side of the septum 704 with the greater septum mass so the slit or perforation 708 shifts toward the midline with septum displacement during insertion in cooperation with the effect of the centering member 720 of the cannula 732. The upper surface 750 of the housing 728 and the upper surface 714 septum 704 can be matched with the outer surface of the cannula 760 and inner surface 780 of the centering member 720 to provide a compression region during forced juxtaposition of these surfaces with insertion.

FIG. 31 a shows an alternative configuration of a septum 800 for use with a mechanically biocidal cannula and septum system of the type similar to that shown in FIG. 31. The upper surface 808 of the septum 800 is matched with the tip 810 of the cannula 814 such the upper surface has a depression 820 with a diameter matched to the diameter of the end of tip 810. The larger slot 830 is larger in its proximal extent to accommodate the central shift discussed above. As shown, the diameter can be but slightly larger prevent fluid from being trapped between the tip 810 and the depression 820 during insertion. The depression 820 can serve as a reservoir for receipt of a projection of a disinfection cap of the type similar to that shown in FIG. 26.

In one embodiment shown in FIG. 32-38 the septum 900 has a proximal slit 904 which extends to a position adjacent the distal end 908 (FIG. 38) of the septum 900 (although, if preferred the slit can extend all of the way through the septum 900). The septum 900 has a distal slit 910 perpendicular (or otherwise angled) with respect to the proximal slit 904. The biocidal cannula 914 (FIG. 32) can be of the type similar to that shown in FIG. 27-29 with opposing distal openings 915 (positioned at the end of flow channel 916) which are aligned, as by matching a cannula guide 917 and a conventional lockable guide on the septum housing (not shown) so that with insertion of the cannula 914 into the slit will cause the openings to be aligned with and communicate with a perpendicular slit 910. The cannula 914 length and the septum 908 length can be matched so that the openings in the cannula 914 line up with opened perpendicular slit 910 when the cannula 914 is maximally advanced with the cannula tip 918 projecting to a point just proximal to the distal end 908 of the septum 904. The cannula 914 can include a conventional locking mechanism such as clips 919 to retain the cannula 914 in an advanced position with the openings 915 aligned with the opened perpendicular slit 910.

When the cannula 914 is fully advanced and locked in position within the septum, the perpendicular slit 910 is separated into two opposing slits 920 and 924, which become divided and separated by the now interposing cannula 914 within slit 904. With the cannula 914 fully advanced and locked in place, the opposing slits 920 and 924 are distorted by the distal end 918 of the cannula 914 into an open position so that the opposing slits 920 and 924 communicate with the opposing openings 915 and the flow channel (not shown) adjacent the distal end 908 of the septum 900. To facilitate the opening of the proximal slit 904, the septum 900 has a first set of slots 930 for receiving displaced septum mass parallel with the proximal slit 904. In addition, to facilitate the opening of the distal perpendicular slits 920 and 924 (along a different transverse axis than the displacement of the more proximal displaced septum mass) a second, more distal set of slots 940 is provided parallel with the perpendicular slits 920 and 924.

In an alternative embodiment (not shown) similar to the above embodiment, the proximal slit 904 can be lengthened to the to extend through the septum end 908 and the opposing distal openings 915 of the cannula 914 can alternatively be aligned (as by matching guides on the cannula and housing) so that, with insertion, the openings 915 are aligned with, and communicate with the distal end of the slit 904, the long transverse axis of slit 904 can be extended to adjacent the end 908 of the septum 900 to accommodate the flow of liquid out the openings 915. In this embodiment, the transverse length of the distal ends of the slit 904 adjacent the distal septum end 908 is longer than the diameter of the cannula 914 so that opposing spaces are opened adjacent the cannula 914 adjacent the end of the slit 904.

Figure 39:
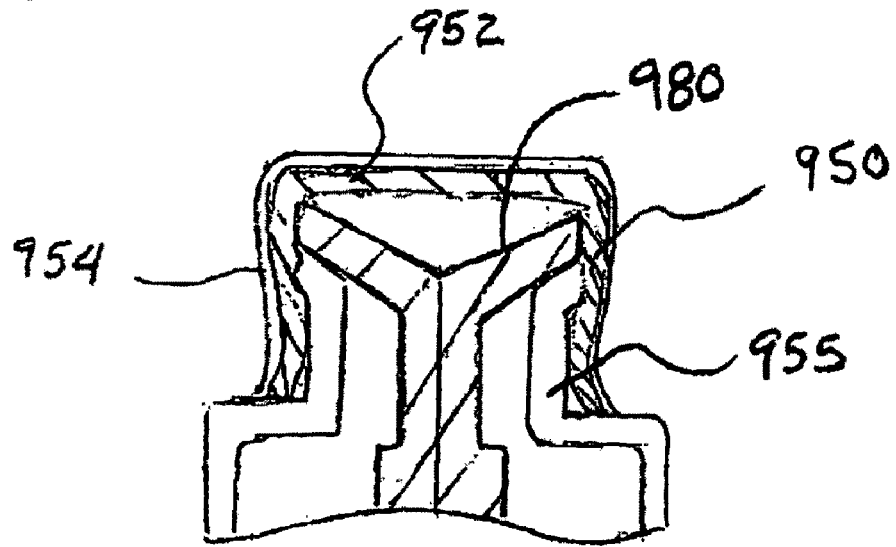
FIG. 39 is a longitudinal section view through a luer receiving valve covered by a Swab Pocket
Figure 40:
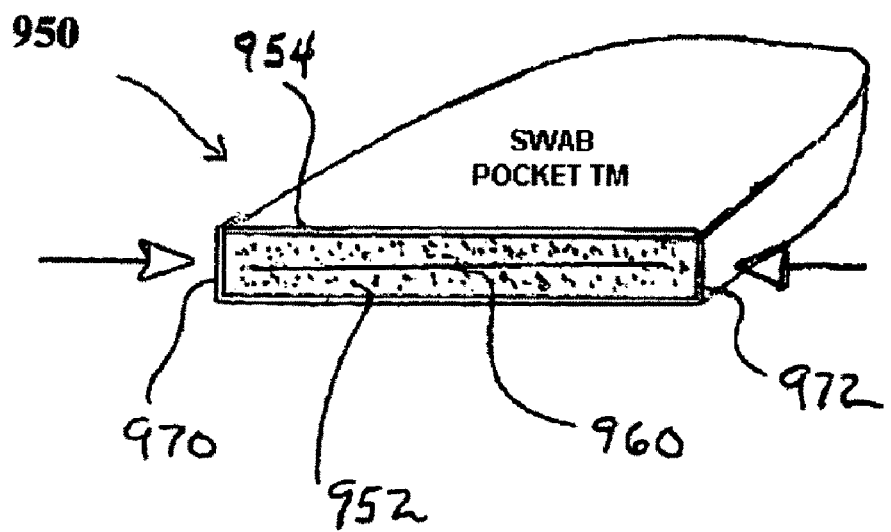
FIG. 40 is a perspective view of a Swab Pocket.

FIGS. 39, 39*a*, and 39*b* show embodiments of a "Swab Pocket™" 950 for reducing MTEs by covering the valves, such as those discussed above. The swab pocket serves as both a valve facial swab and a valve cover. Unlike conventional swabs, the swab pocket is preferably applied after the cannula or luer has been removed from the valve. In one embodiment, the swab pocket 950 includes an absorbent inner layer 952 preferably comprised of elastic fabric or otherwise the swab pocket may be non-elastic and comprised, for example, of a thin layer of absorbent cotton with an outer layer 954, which can for example be comprised of polyethylene terephthalate. (This material is in wide medical use and is sold for example in combination with cotton under the trade name Telfa). Alternatively, other suitable medical grade material which is at partially impermeable to reduce evaporation of disinfectant liquid (if an evaporable liquid is used) from the swab pocket 950 may be used and the proximal end of the outer layer 954 may curl in to cover the proximal end of the inner layer 952 to further minimize evaporation.

Figure 24:
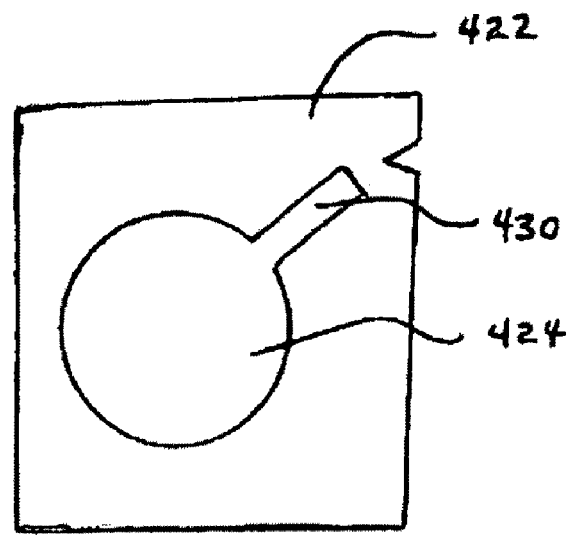
FIG. 24 is a top view of a disposable anti infective cap insert within its package.

In one embodiment the swab pocket 950, has an open-able end 960 and the swab pocket 950 is packaged in a clear package such as that shown in FIG. 24 with the open-able end 960 in a closed configuration. During operation the sides 970 and 972 of the swab pocket 950 are squeezed (as indicated by the arrows) to open the open end 960 of the swab pocket 950 for insertion over a valve. The absorbent inner layer 952 preferably contains a chemical disinfectant such as, for example chlorhexidine with or without alcohol, or an iodaphor. A separate or attached absorbent insert or other reservoir of disinfectant (discussed below) can be provided within the swab pocket 950 if desired. It is preferable for the disinfectant to have a low volatility or can be mixed with or covered by a substance of low volatility such medical grade silicone oil (of the type used for example to lubricate syringes) to enhance retention. Medical grade silicone oil has the added value of providing a lubricant to reduce penetration force despite compression. This simple swab pocket 950 provides a very inexpensive self securing cover which functions to protect a valve from contact contamination or droplet nuclei and also functions to provide a ready source of disinfectant at the face 980 (FIG. 39*b*) of a valve 955. One of the purposes of this invention is to provide a very simple cover which is so inexpensive that it can be implemented in countries or hospitals which lack the resources to accommodate the considerable additional expense associated with the uses of more robust caps for all access sites. This embodiment can provide this enhanced protection, and serve as a continuous reminder to swab because it is already in place and must be removed to access the device. According to the present invention, these functionalities can be achieved, for a cost which does not greatly exceed the cost of the conventional prepackaged chlorhexidine disinfectant swab itself.

In an embodiment a swab pocket 978 has at least one elastic component which can, for example be an integral, insert molded, bonded or otherwise attached, elastic band 974 (FIG. 39*a*) located adjacent the open end of the swab pocket 978. Alternatively, the entire swab pocket 978 may be elastic or the swab pocket outer layer 954 may be elastic. The swab pocket 978 can include or be comprised of another component with shape memory, such as, for example, an outer layer 954 comprised of elastomeric material integral, bonded or otherwise attached to an inner layer or component which contains disinfectant. The outer layer can for example be an optically clear elastic silicone sleeve, coating or molded component. The outer layer can for example be molded with the fabric or molded into the fabric. Alternatively the entire swab pocket may be comprised of an optically clear elastic silicone and/or of material with elastic shape memory such as the moldable elastomere sold under the trade name Zello™ marketed by Zeller International with an internal pocket containing releasable disinfectant.

As shown in FIG. 39*b* an internal pocket 948 can for example include an insert molded sponge or fabric 950 at the blind end 952 of the swab pocket 954. In an example, the swab pocket 954 may be may be molded woven for formed with the insert 950 in the internal pocket 948 (such as cotton) adjacent the inner surface of the blind end 952 of swab pocket 954 for containing the disinfectant The insert 950 may be covered with a thin layer 958 of water resistant material such as silicone having perforations or through serrations 960 so that disinfectant is released through the perforations or serrations 960 upon digital pressure applied against the top 953 of the swab pocket 954. Alternatively, the outer layer 961 of the swab pocket can be comprised of optically clear elastomere. The outer layer 961 can be integral or otherwise engaged (as for example bonded) to at least a portion of the swab pocket 954, so that the swab pocket 954 can be secured to the valve 962 by the shape memory and/or elastic rebound of the swab pocket 954 without the need for the covering flip cap 400 (FIG. 26) or other cover or cap.

Alternatively the swab pocket 954 can be packaged in a more "open pocket shape" with a distal opening being slightly closed or slightly open. The swab pocket 954 can comprise a narrow neck with or without an enlarging distal end to provide a shape memory to providing tight engagement with the valve while allowing easy insertion over the valve. The neck or opening can be squeezed at the time of application over the valve to open it or enlarge the opening. The tight elastomeric neck with an enlarged distal end allows for a generally universal secure attachment to different shaped valves. The tight neck may also be employed to reduce the potential the loss of a volatile disinfectant (if employed).

In an alternative embodiment the swab pocket is comprised entirely of non elastic material. In an example the inner layer can comprise a thin layer of absorbent cotton impregnated with a chlorhexidine alcohol mixture or and the outer layer, can be comprised of polyethylene terephthalate. The swab pocket may be specifically formed to fit over a specific valve shape. A tether, latch or other connecting member may be provided for securing the swab pocket to the valve.

In another embodiment a slit 970 (FIG. 39*a*) may be provided adjacent the open able end 972. The slit 970 may have at least one elastic portion 974 for receiving the branch of a y-site (not shown) and for elastically holding the swab pocket 978 over the branch of a y site to secure the valve to and over the y site.

In another embodiment (not shown) a facial covering is provided (which can be a swab pocket for attachment by the user or can be applied during manufacture). The facial covering is left in place for 72 hours or is permanently attached. The covering has a slit or perforation for receiving the luer tip or blunt cannula with the walls defining the slit in the swab pocket sealed or otherwise bonded so that portions of fabric cannot be displaced by the advancing luer or cannula. In one embodiment the fabric is about 2-3 mm adjacent the central slit so that the pressure of the luer against the swab pocket immediately before and during insertion increases the release of disinfectant from the fabric. The disinfectant from other portions of the fabric then diffuses into the portion adjacent the slit. If preferred, fabric or sponge containing disinfectant can be onset molded or otherwise provided into or with the septum so that disinfectant is released on pressure during luer insertion.

Figure 41:
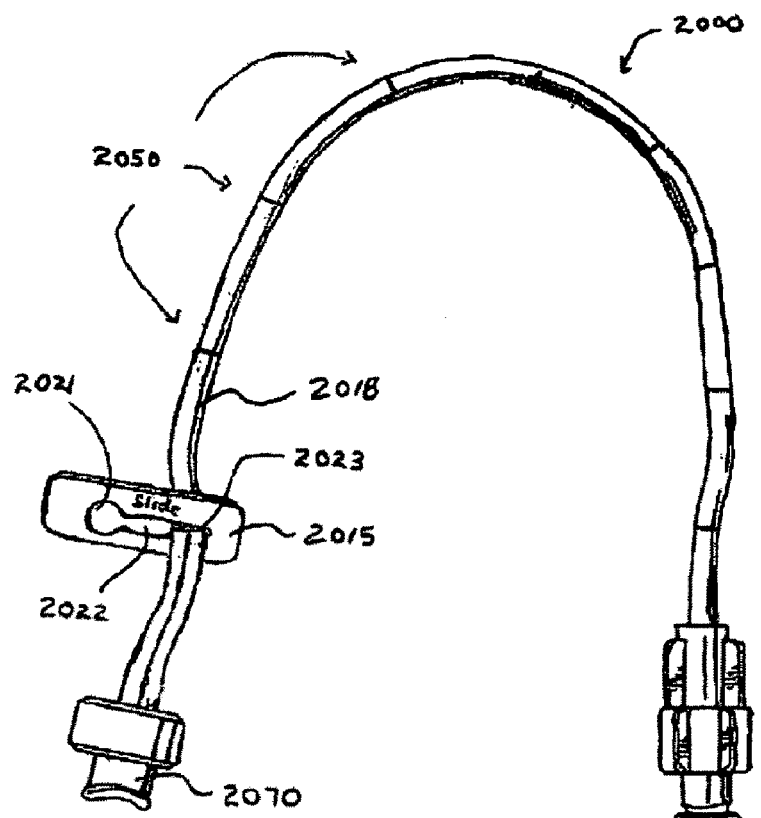
FIG. 41 is a top view of one embodiment of the Catheter Flushing Extension Set which employs pinch reservoirs.
Figure 41A:
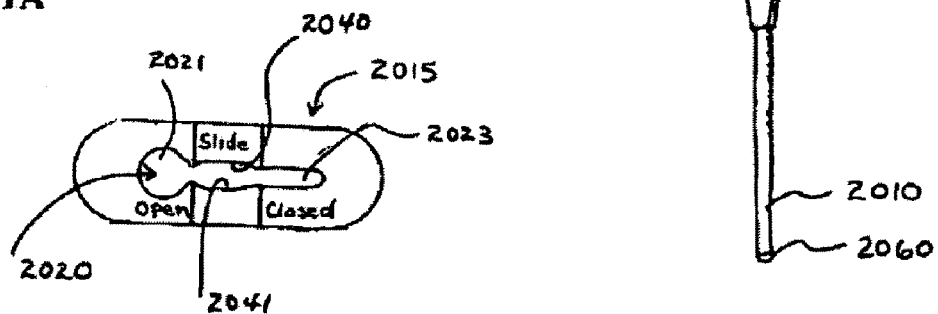
FIG. 41a is a top view of a catheter flushing slide.

FIG. 41 shows an catheter flushing extension set 1000 similar to that disclosed in U.S. patent application Ser. No. 10/533,749 of the present inventor, the contents of which are incorporated by reference as if completely disclosed herein, for use with an indwelling catheter 1010 and which is designed to both reduce the number of accesses as well as the MTE % and MTE Magnitude. The catheter flushing extension set 1000 is shown with a short length of tubing 1011 (which can be comprised for example of silicone) with a plurality of flexible pinch reservoirs 1012, 1014, 1016 which can be reversibly moved from the open to closed position. The reservoirs have a stable closed position so that once they are pinched they remain closed until re-inflated. Each time one of the reservoirs 1012, 1014 or 1016 is closed the fluid from that reservoir squirts out the catheter tip 1020 and flushes it. The catheter flushing extension set 1000 can have 9 reservoirs or more if desired so that all flushing over a 72 hour period can be accomplished by closing reservoirs rather than by attaching an external saline flush syringe. The reservoirs 1012, 1014, 1016 are readily reopened by occluding the tubing by digital pressure adjacent the catheter hub 1030 and then injecting saline into the system essentially popping open the reservoirs 1012, 1014, 1016. The proximal terminal 1032 is preferably closed by an attached biocidal septum 1034 so that, in addition to reducing the number of accesses (and therefore the number of MTEs) the catheter flushing extension set 1000 can also reduce the MTE % and MTE Magnitude. The implementation of the catheter flushing set 1000 hospital wide can also result in considerable savings by eliminating the need for a large percentage of the pre-filled saline flush syringes (which are expensive to employ in high numbers).

Figure 42:
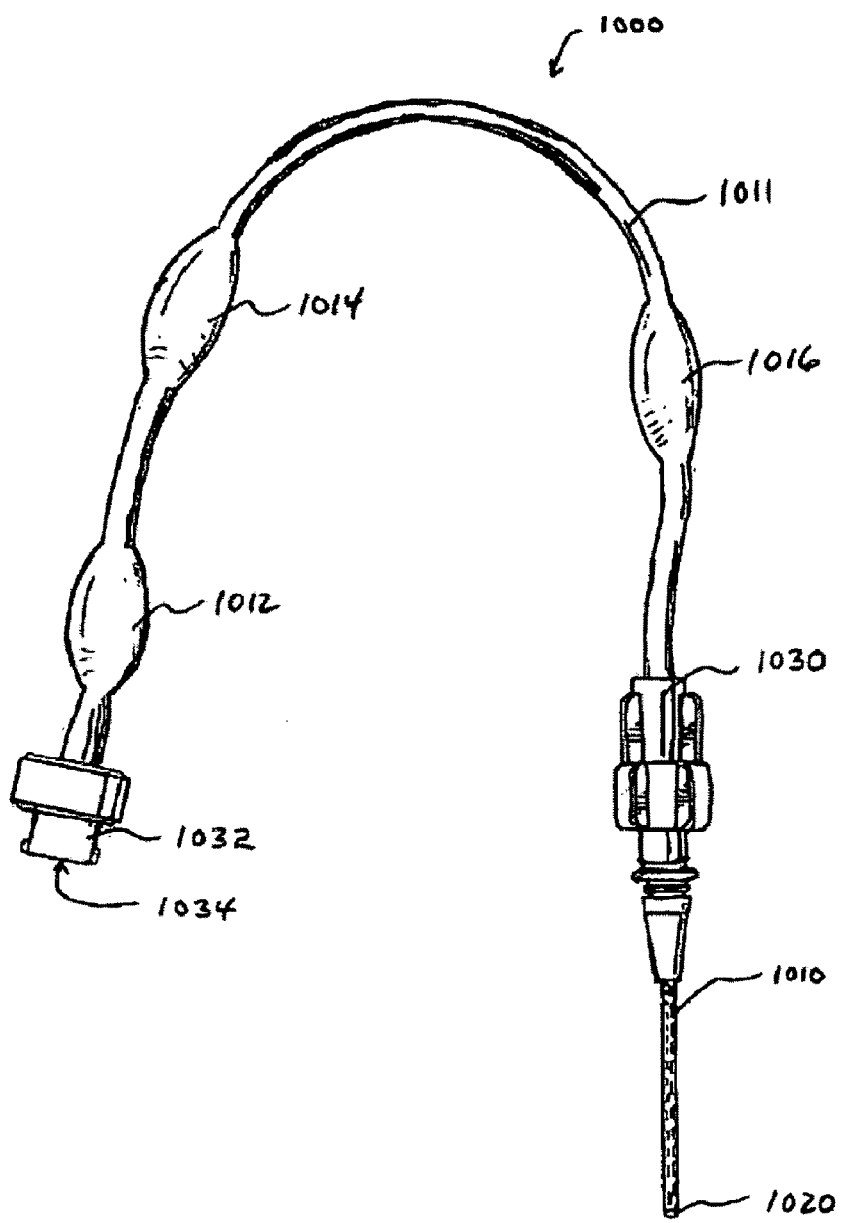
FIG. 42 is a top view of one embodiment of the Catheter Flushing Extension Set which employs a catheter flushing slide.

FIG. 42 shows another embodiment according to the present invention of catheter flushing extension set system 2000 similar to that disclosed in US patent application for use with an indwelling catheter 2010 and which is designed to both reduce the number of accesses as well as the MTE % and MTE Magnitude. The extension set 2000 is shown with a catheter flushing slide 2015 which can be reversibly moved along the tubing 2018. The catheter flushing slide 2015 has a tubing receiving slot 2020 with three regions (positions) for receiving the tubing 2018; an open position 2021, a slide position 2022, and a locked position 2023. Each of the regions on the slide 2015 around each position may be color coded or otherwise well marked with the region around the open 2021 being, for example green, the region around the slide position 2022 being yellow, and the region around the locked position 2023 being red. The slide 2015 is preferably comprised of plastic with very slick opposing surfaces 2040 and 2041 of the open position for sliding engaging the tubing 2018 to produce peristaltic forward movement of the fluid in the segment. The slide 2015 may for example have a lubricating coating on at least the opposing surfaces 2040 and 2041 slide portion. The tubing 2018 has marks 2050 along the tubing 2018 to designate each new, more advanced sliding flush position. The tubing 2018 preferably has a low rebound force so that a substantial vacuum does not develop in the tubing 2018 after the slide 2015 has been slid along the tubing 2018 and a significant portion of the tubing is in a closed position state. Each time the slide 2015 is advanced the fluid from the segment of tubing 2018 compressed by the slide 2015 squirts fluid out the catheter tip 2060 and flushes it. The catheter flushing extension set 2000 can have 9 slide positions (marks) for the slide 2015 or more if desired so that all flushing over a 72 hour period can be accomplished by advancing the slide 2015 rather than by attaching an external saline flush syringe. The catheter flushing extension set 2000 can be refilled with saline by attaching a pre-filled syringe to the access port 2070 and injecting saline, this expands the tubing 2018 proximal the slide 2015. The nurse then moves the slide 2015 to the open position 2021 and continues to inject saline so that the tubing is full of saline (or other flush solution) and so that no reflux of blood into catheter tip 2060 occurs during the tubing 2018 refilling process. If a piggy back infusion is due and no prior flush is planned then the piggy back is connected to the portal 2070 and opened to open the tubing 2018 proximal the slide 2015 then the slide is moved to the open position 2021. According to the invention, other means for causing flushing from a plurality of extension set segments such as, for example a moving peristaltic roller, with for example two opposing rollers held by a small graspable housing and movable along the tubing (and compressing the tubing between the rollers with each advancement) can also be employed in a similar fashion to that described for the slide discussed above.

FIG. 42a shows an integrated self flushing catheter with side mounted tubing and a slide of the type shown in FIG. 42.

Figure 43:
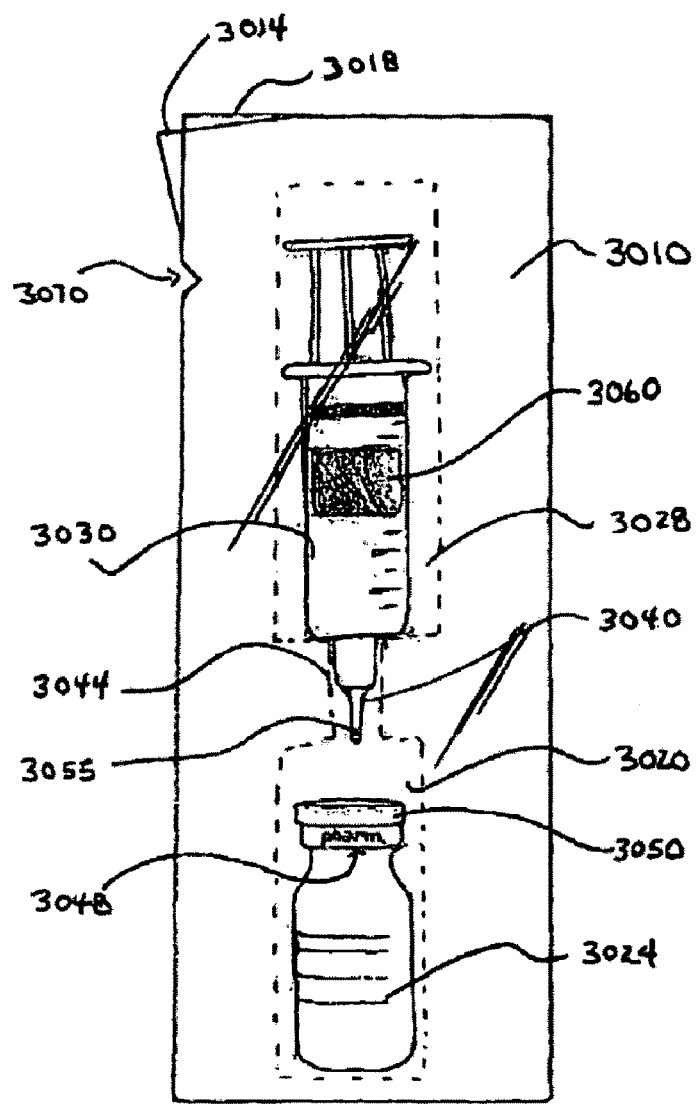
FIG. 43 is a top view of a pharmaceutical mixing packaging system which includes a pre filled syringe.

FIG. 43 shows a syringe packaging system 3000 which comprises another embodiment intended to reduce MTEs by reducing contact contamination of the biocidal cannula and also intended to provide enclosed mixing of a diluent and pharmaceutical which reduces nursing exposure to the pharmaceutical and further reduces the potential for contamination of the mixture during the mixing process. The syringe packaging system 3000 can be of the type described and claimed in U.S. Pat. No. 5,769,825 entitled. "Self-contained syringe and pharmaceutical packaging system for enclosed mixing of pharmaceutical and diluent" of the present inventor, the contents of which are incorporated by reference as if completely disclosed herein, As shown in FIG. 43 an outer package 3010 comprises two opposing and bonded layers, an upper clear layer 3014 and a lower layer 3018 which may be opaque or clear. The layers are separated in region to defining a lower chamber 3020 which contains a capped pharmaceutical vial 3024 containing a pharmaceutical agent and an upper chamber 3028 which contains a pre filled syringe 3030 having a selected pre-filled volume which is matched to provide the proper dilution of the agent in the vial 3024. The syringe 3030 has a biocidal cannula 3040 attached with a tip projecting into a pathway 3044 (which can define a cylindrical portion). The drug vial septum 3048 is covered with a thin plastic cap 3050. The septum 3048 is configured such that the tip 3055 can penetrate the septum 3048 of the drug vial 3024. In an alternative configuration (not shown) the septum 3048 can incorporate the tip of the cannula or the tip of the luer end of the syringe by molding the tip of cannula or luer end of the syringe in a position partially through the septum or by pre inserting tip of cannula or luer end of the syringe partially through the septum and fixing it in that position during or before packaging. This allows ready penetration into the drug vial. The pre-filled diluent syringe 3030 can be similar in configuration to the type marketed by the Becton Dickinson under the trade name Posiflush. The short, squat configuration of the Posiflush syringe, and the short extension length of the syringe with the withdrawn piston, facilitates efficient and compact packaging with the drug vial and operation within the enclosed package.

In operation the little plastic cover cap 3050 over the septum 3048 of the drug vial 3024 is removed by grasping it through the package 3010 and allowed to fall inside the lower chamber 3020 adjacent the vial 3024. If a cannula cap (not shown) is present over the cannula 3040 this is also removed by grasping it through the package 3010. The drug vial 3024 and syringe 3030 are then advanced together to cause the cannula 3040 to enter the inner chamber of the vial 3024. A small amount of air is withdrawn into the syringe 3030 from the vial 3024, if desired, to minimize pressure build up in the vial 3024. With the vial 3024 held with any aspirated air near the plunger 3060, the diluent is then injected into the vial 3024. The vial 3024 and the attached syringe 3020 are shaken as a single unit. The entire package 3010 is held so that the vial 3024 is on the top and the mixture is aspirated into the syringe 3010. The entire package 3010 is then taken directly to the bedside (if the entire procedure was not performed at the bedside) and then opened at the pre tear site 3070 and the syringe 3030 is removed and connected directly to the biocidal cannula 3040 for injection.

The combination of enclosed drug and diluent mixing with the use of a biocidal septum and cannula provides for protection against contamination during each sequential process of drug delivery which is particularly useful with medication provided in the home or in a vulnerable population such as bone marrow transplant recipients or patients receiving chemotherapy. The enclosed mixing also has the advantage of greatly reducing exposure of the nurses to aerosols or other means of occupational chemotherapy exposure. The biocidal cannula and biocidal septum have many additional uses and can be provided in substantially any environment or system wherein fluid access into a patient's body is desired.

In an alternative embodiment the pre-filled syringe and drug vial can be shrink wrapped together in alignment with a small flexible cylindrical channel between for advancing the cannula when engagement is desired. The shrink wrapping can help prevent inadvertent advancement. For storage the package and its connecting cylindrical portion can be flexed so that the syringe and vial are stored and secured to each other side by side for ease of standing in typical hospital drug storage containers. When mixing an injection is desired, the package is carried to the bedside, the wrapped syringe and vial are straightened from their side by side flexed position into alignment, and the procedure described above performed.

Figure 1:
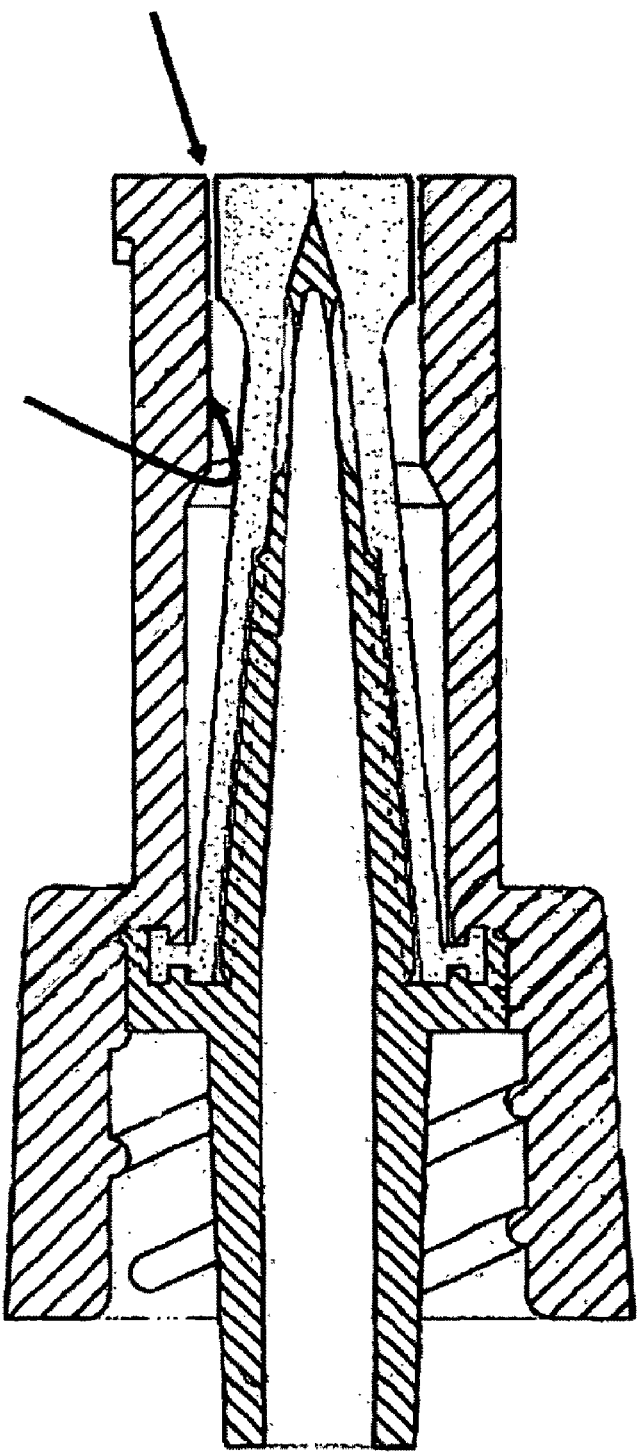
FIG. 1 is a center section view of a piston luer valve of the prior art.
Figure 2:
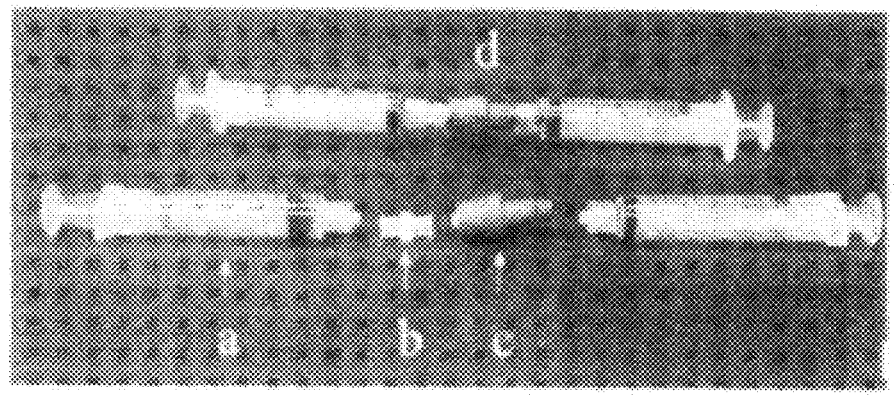
FIG. 2 is a photograph of a piston luer valve of the prior art disconnected and connected to the luer at the end of a syringe
Figure 3:
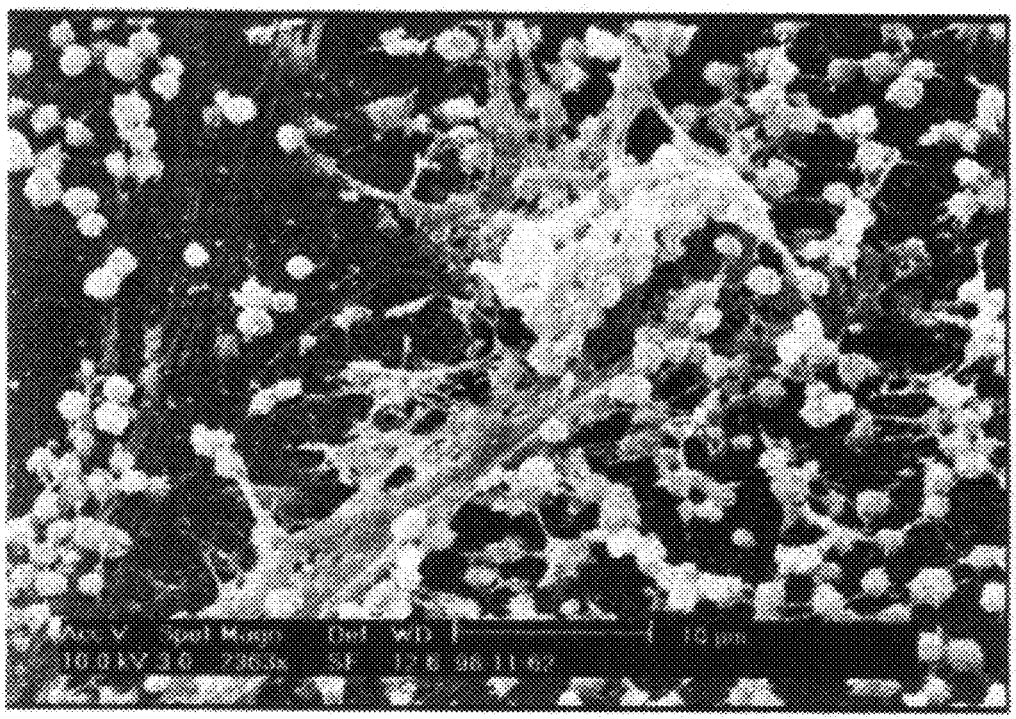
FIG. 3 is an electron micrograph from a study performed by the Center for Disease Control showing bacteria and biofilm residing within the circumferential space of the piston luer valve of FIG. 2.
Figure 4:
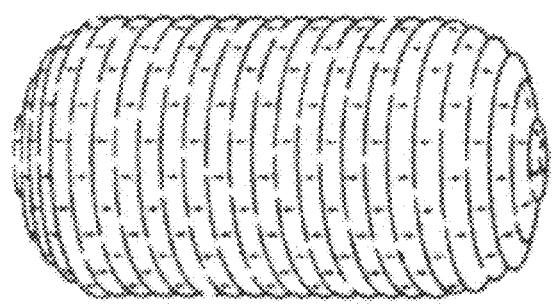
FIG. 4 is a background schematic of a bacterium depicting the outer three-dimensional elastic stress bearing elastomeric sacculus which retains the internal fluid.
Figure 5:
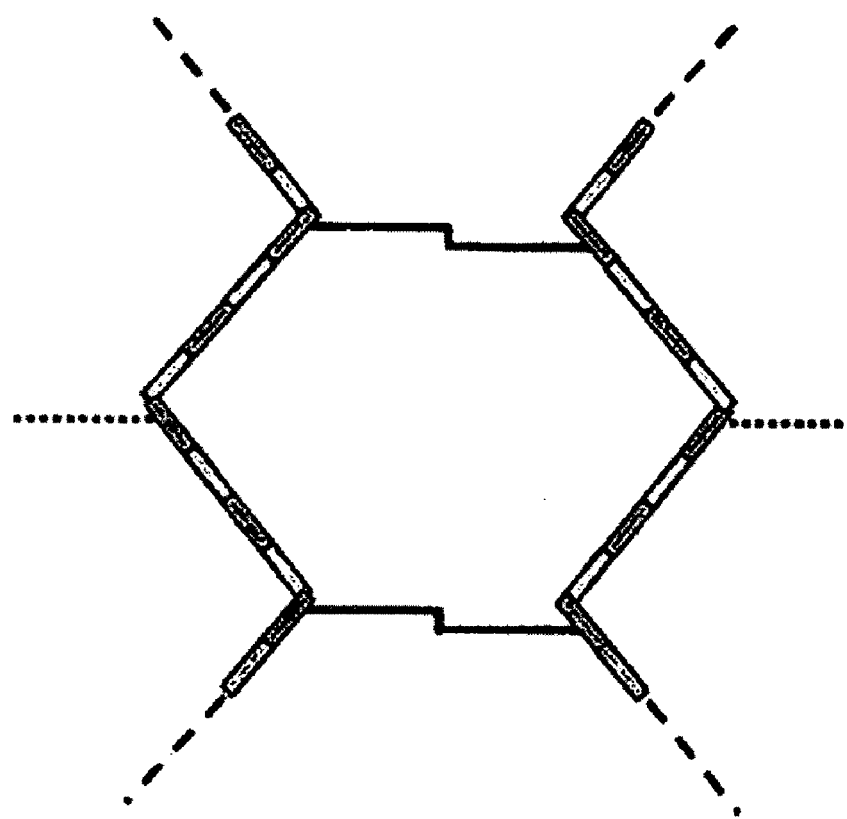
FIG. 5 is a background schematic of the biologic elastomer, peptidoglycan showing the fundamental Tessera unit which repeats to form the elastic macromolecule. Note the striking structural similarity of the biologic elastomer of the cell wall to a cross-linked molecular structure of a silicone elastomer, which, according to the present invention is used to mechanically destroy or displace the elastic macromolecule peptidoglycan.
Figure 44A:
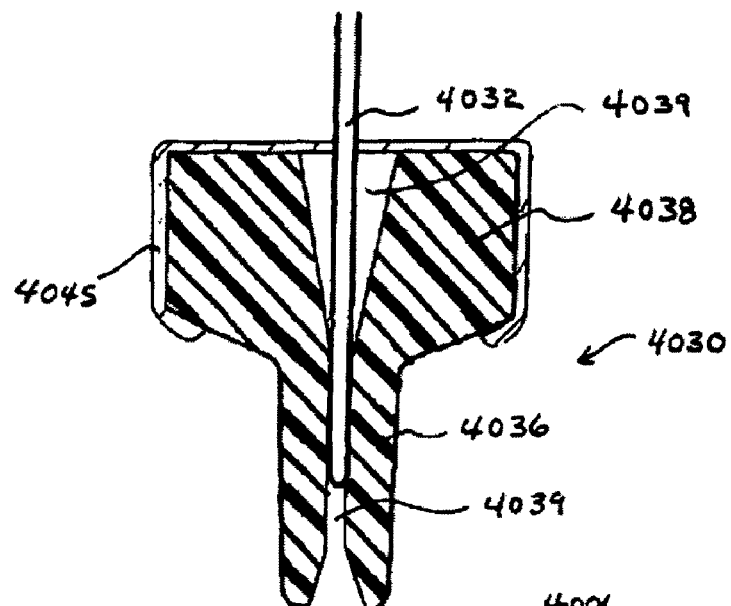
FIG. 44a is a longitudinal section view of a luer valve adapted introducer according to the present invention.
Figure 44:
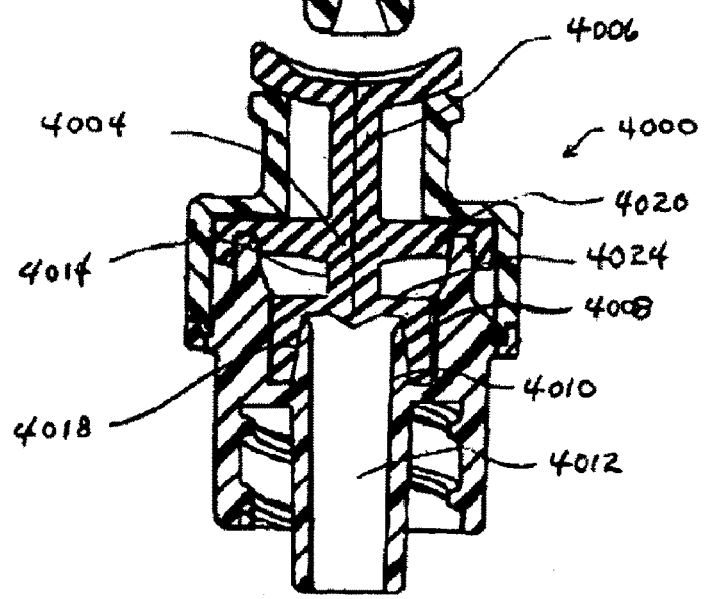
FIG. 44 is a longitudinal section view of a luer receiving valve according to the present invention

FIG. 44 shows a closed bloodless catheterization system intended to reduce MTEs during catheterization and to reduce the risk of air embolism and reduce hospital worker blood exposure during catheterization. In one embodiment, the luer receiving valve 4000 for receiving a male luer 110 of a luer lock connector (shown in FIG. 11) is permanently attached to a peripheral catheter (for example of the type shown in FIG. 42), a central venous catheter, femoral catheters, picc, midline catheter or other catheter so that inadvertent disconnection (with attendant deadly silent air embolism and bleeding) is reliably prevented. The valve 4000 can be provided at the proximal terminal of a cardiac or other diagnostic or interventional catheter introducer for femoral, brachial, jugular, subclavian, or radial catheter, for example for stent, guide wire, or diagnostic catheter introduction (to name a few). The luer receiving valve 4000 is similar in configuration to that shown for example in FIG. 2 of U.S. Pat. No. 6,908,459 and in various figures of U.S. Pat. No. 6,171,287, the contents of which are incorporated by reference as if completely disclosed herein. However, the lower portion 4004 of the septum 4006 is modified to form an outer elastomeric tube 4008 for intussusception over an inner tube 4010 about the flow channel 4012. The length of the downwardly projecting septum 1014 is greater than the length of the male luer 110 (FIG. 11) so that negative pressure is mitigated or eliminated upon withdrawal of the luer from the septum. The outer wall 4018 of the inner tube 4010 can be upwardly tapering to facilitate insertion of the outer tube 4008 over the inner tube 4010. If desired support columns (not shown) may be provided between the proximal portion 4020 and the distal septum portion 4024 of the lower septum portion 4004. The outer tube 4008 may be securely held about the inner tube 4010 by tight wedging, by adhesive, or by an overhanging ledge or projection (not shown) above the distal portion 4024.

Figure 45:
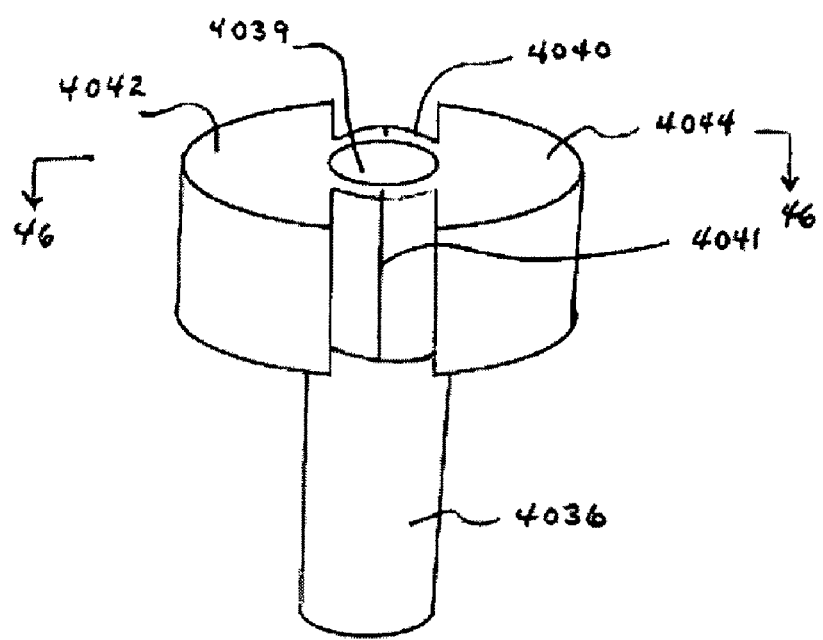
FIG. 45a is a perspective view of a luer valve adapted introducer according to the present invention.
FIG. 45b is a perspective view of a luer valve adapted introducer according to the present invention in the flexed position.
Figure 45:
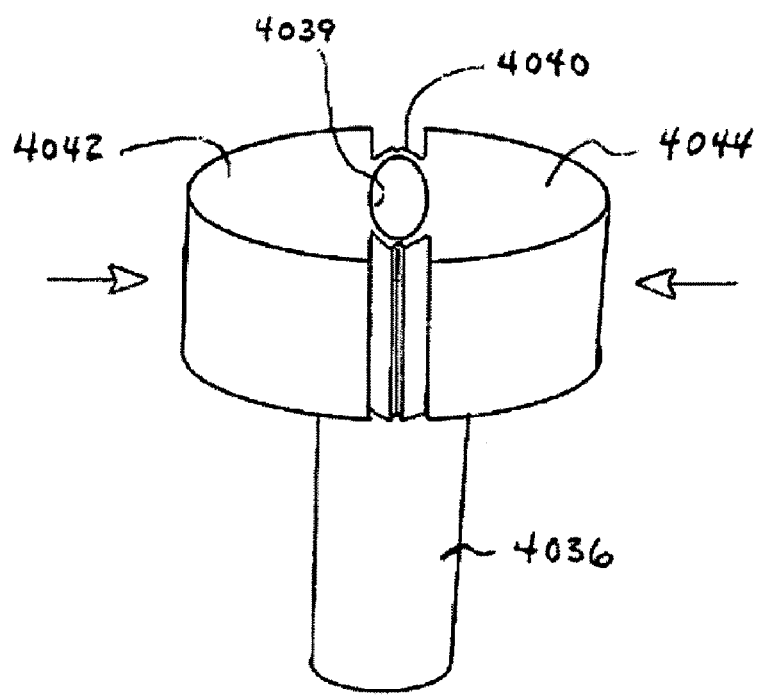

In FIG. 44a, a luer receiving valve adapted introducer 4030 is provided for receiving the guide wire, diagnostic catheter or devices, or interventional catheter or devices collectively illustrated as elongated implement 4032. The valve adapted introducer 4030 has a distal projecting member 4036 (which can be configured to have the outer dimensions of an ANSI standard male luer) and a handle 4038 and a lumen 4039 extending through the projecting member 4036. Although not shown in this figure, if desired, the valve adapted introducer 4030 can have a downwardly projecting luer lock portion (of the shown in FIG. 11) for threading in and out of fluid connection with the flow channel 4012. The withdrawal or threading out maneuver will allow the distal septum portion 4024 to rebound about the elongated implement 4032 to stabilize the elongated implement 4032 in a fixed position. The handle 4038 of the valve adapted introducer 4030 provides an upper funnel opening 4039 for receiving the elongated implement 4032. As shown in FIGS. 45a and 45b, the opening has a thin wall 4040 with opposing slits 4041 so that opposing semicircular sides 4042 and 4044 can be flexed towards each other by compression (as by the thumb and finger along the axis shown by arrows in FIG. 45b) and then moved back to the non-flexed position by rebound or by applying pressure perpendicular to the flexing pressure. If preferred the valve adapted introducer 4030 can be modified so that both the flexed and non-flexed positions are stable so that the elongated implement 4032 can be either readily movable or fixed depending on whether the handle is in the non-flexed or flexed position. In FIG. 44a, the handle 4038 is covered with an optional elastomeric boot 4045.

The valve adapted introducer 4030 are preferably configured to engage the valve 4000 such that a guide wire being withdrawn through an attached catheter (as during insertion or exchange of the catheter by the "over the guide wire" technique) will be funneled into the valve 4000 and/or the luer valve adapted introducer 4030 rather than becoming caught along the flow channel 4012.

The luer valve adapted introducer allows performance of a method of closed catheterization. An example follows: When a catheter (for example a multi-lumen catheter) having attached valve(s) at the terminal(s) is being inserted by this closed catheterization method, a luer end of a syringe containing saline (with or without an anticoagulant) is first inserted into each the luer valve and each lumen is flushed. The needle is then inserted into a blood vessel and a guide wire advanced into the vessel. The luer valve adapted introducer is inserted into the valve and the catheter fed over the guide wire in the usual way. The luer valve adapted introducer assists in guiding the wire through the valve and out the luer valve adapted introducer where it is grabbed and the catheter is then advanced to the desired position in the vein over the wire. The wire is then removed and a syringe with a male luer is advanced into the valve, the lumen is checked for residual air by aspiration and then the distal lumen is flushed. The entire process is carried out without atmospheric exposure of the interior of the valve, the lumen, or the blood vessel.

In another example, a conventional outer cardiac catheter introducing catheter (also called an "introducer") is provided in the sterile package with a fixed luer valve in place which may be integral with the outer introducing catheter. The outer introducing catheter is inserted (for example into the femoral vein) using the closed catheterization method described above. A luer valve adapted introducer with a lumen sized for diagnostic and/or interventional cardiac catheters is positioned over the end of the cardiac catheter (or may be provided with and previously mounted over the cardiac catheter). The luer valve adapted introducer and the catheter can be inserted together or the luer valve adapted introducer can be inserted first and then the cardiac catheter inserted through it. The procedure is then carried out, when catheter fixation is desired this can be achieved by flexing the handle of the luer valve adapted introducer or by withdrawing the luer valve adapted introducer partially from the luer valve (as discussed above). On catheter exchange there is no bleed back or risk of air embolism since the lumen of the indwelling outer cardiac catheter introducer is never opened. When the procedure is completed, or if desired during the procedure, the cardiac catheter can be removed and blood at very high flow rate or rapid high volume fluid resuscitation can be immediately administered without opening the system though a luer inserted into the valve. The procedure can then be restarted again without opening the system. If a side port is provided on the outer cardiac catheter introducer with a fixed luer valve fluid can be administered at the same time the procedure is being performed. Again all of this can be performed without opening the system in the conventional manner. This same technique can be applied to vascular catheterization for angiography or vascular stent placement. For some elongated implements such as a diagnostic cardiac catheter the desired internal lumen of the luer adapted introducer may be much smaller than that of a conventional luer. For large interventional devices it may be desirable to have an internal lumen within the luer valve adapted introducer larger than that of a conventional luer. A finely adjustable lumen diameter, as can for example be provided by a compressible touy boyst fitting (touy boyst fitting are well known in the art), mounted in the handle of the luer valve adapted introducer can be provided if a single luer valve adapted introducer is desired for a wide range of catheters.

FIG. 46 shows a modified valve 4050 with a second elastomeric tube 4055 projecting within a rigid inner tube 4060. The second elastomeric tube 4055 serves to guide the guide wire through the valve 4050, to further stabilize the distal septum portion 4065 against downward deflection, and to minimize deadspace.

As noted, the ability to easily introduce a guidewire or other elongated medical implement through a permanently or near permanently fixed valve sealing the proximal end of a catheter or introducer greatly reduces the risk of air embolism and hemorrhage due to inadvertent disconnect. In addition, all of this is accomplished while maintaining a closed system throughout the procedure of catheter insertion, catheter exchange, cardiac catheterization, or any of a wide range of diagnostic and interventional procedures involving the vasculature or other internal body accesses (such as ureteral catheterization). Another advantage of this approach is that the luer valve access terminal, through which the cardiac catheterization for example is being carried out, is immediately available at any time during or after the procedure for the closed administration of very high flow blood and other fluids through the luer valve without the need for disconnection or opening the system or insertion of another large bore catheter. A final advantage is that the valve never does need to be removed for insertion, guide wire exchange, repositioning, or for insertion of diagnostic or therapeutic implements so that the catheter terminal is never opened and exposed to the atmosphere in the conventional manner associated with removal of the valve or with insertion without the valve in place. In an example of the degree with which this maintains a closed system a multi-lumen catheter can be provided in the sealed package with valves secured and closing all terminals, and the catheter can be inserted using the over-the-wire technique without removing a single valve by inserting the wire through the valve in fluid connection with the distal lumen.

FIG. 47 shows a two part Luer Access Device disinfecting system 5010. The system comprises a pair of conjoined packages 5011 and 5012. The packages are selectively detachable from each other via perforation 5013. Further, each package has notches 145014 and 5015 designed to indicate to users where to open the package. Notches 5014 and 5015 also serve to selectively weaken the package in such a manner that users can tear the package open manually. Indices, 5016 and 5017 are provided in order to designate a visual difference between the two packages and their contents.

FIG. 48 is a cutaway view into system 5010 wherein swab 5018 and swab pocket 5019 can be seen isolated each from the other. In accordance with standard alcohol wipe type products the packages 5011 and 5012 also hold a measure of liquid disinfectant 5012 which liquid disinfectant also saturates the devices therein.

The method of use is to open and remove swab 5018, designated as "Part 1", from package 5011. Apply the disinfectant solution from swab 5018 to the surfaces of a LAD. Then access the LAD and administer fluids or medicaments as required. Following injection, package 5012, labeled as "Part 2", is opened and swab pocket 5019 is removed. The outer surface of the swab is rubbed against the surface of the LAD to apply both frictional cleansing and disinfectant solution from swab pocket 5019 to the surfaces of the LAD previously accessed. The swab pocket 5019 is then advanced over the LAD to cover the LAD so that swab pocket 5019 remains in place to protect the LAD from contamination between accesses.

Although the presently preferred embodiments have been described, it will be obvious to those skilled in the art that various changes and modifications can be made without departing from the invention. While the invention has been described in connection with what is presently considered to be the most practical and preferred embodiments, it is to be understood that the invention is not to be limited to the disclosed embodiments.

The invention claimed is:

1. A system for enhancing safety of a patient having an indwelling intravenous catheter comprising:
   a. a luer valve having a swabbable face for receiving a male luer, the luer valve further having a proximal end with an externally threaded portion defining a first diameter for receiving a matching internally threaded shroud of a luer lock connector adjacent the swabbable face, the luer valve further defining a body portion proximal the externally threaded portion, the body portion having an outer wall defining a second diameter greater than the first diameter, and b. a sterile cover sized to be mounted over the swabbable face and the entire externally threaded portion, and at least a portion of the body portion, the sterile cover defining an opening, the opening being sized so that the opening is forcibly dilated by the body portion when the sterile cover is mounted over the body portion, to thereby contact said outer wall of the body portion.

2. A system for enhancing safety of a patient having an indwelling intravenous catheter comprising:

a. a luer valve having a swabbable face for receiving a male luer, the luer valve further having an proximal end with an externally threaded portion defining a first diameter for receiving a matching internally threaded shroud of a luer lock connector adjacent the swabbable face, the luer valve further defining a body portion proximal the externally threaded portion, the body portion having an outer wall defining a second diameter greater than the first diameter, and b. a sterile cover sized to be mounted over the swabbable face and the entire externally threaded portion, and at least a portion of the body portion, the sterile cover defining an elastic opening, the elastic opening being sized so that the elastic opening is elastically dilated when the sterile cover is mounted over the body portion, the elastic opening rebounding to elastically grip the outer wall of the body portion so that the sterile cover is snuggly retained over the swabbable face, the externally threaded portion, and at least a portion of the body portion.

3. The system according to claim 2 wherein the cover is flattened in its stored configuration.

4. A system for enhancing safety of a patient having an indwelling intraveneous catheter comprising:

a luer valve, the luer valve being of the type configured to receive a luer lock connector having a threaded shroud, the luer valve having a swabbable face for receiving a male luer, the luer valve further having a proximal end with an externally threaded portion defining an ISO standard first diameter for receiving a matching ISO standard internally threaded shroud of the luer lock connector adjacent the swabbable face, the luer valve further defining a body portion proximal the externally threaded portion, the body portion having an outer wall defining a second diameter greater than the first diameter; and a device for covering and protecting said luer valve, said device comprising a sterile cover defining an opening sized for receiving the swabbable face, the externally threaded portion, and the body portion, the sterile cover being sized so that outer walls of the sterile cover are forcibly dilated by the body portion when the sterile cover is mounted over the body portion so that the cover grips the outer wall of the body portion and is self-retaining upon the body portion, the sterile cover being further sized so that, in the mounted position, the sterile cover is snugly retained over the swabbable face, the externally threaded portion, and the body portion, with the inside surfaces of the outer walls of the sterile cover in gripping contact with said outer wall of the body portion.

5. The system of claim 4 wherein the sterile cover is comprised of elastic material so that the dilation is opposed by elastic rebound.

6. The system of claim 5 wherein the sterile cover is configured so that elastic rebound secures the sterile cover to the body portion and retains the sterile cover over the luer valve.

7. The system of claim 4 wherein the sterile cover is configured so that it has a flattened configuration when stored.

8. The system of claim 4 wherein at least a portion of the sterile cover is comprised of fabric.

9. The system of claim 4 wherein the sterile cover, adjacent the opening, is comprised of a soft elastomeric material which is capable of dilating to accommodate a range of diameters so that the sterile cover is securely self-retaining upon a range of different luer valve body portions.

10. The system of claim 4 wherein the sterile cover is comprised of an absorbent material and a water resistant material.

11. The system of claim 4 wherein the sterile cover defines an inner pocket containing a disinfectant.

12. The system device of claim 4 wherein the sterile cover defines a wall and the wall provides a receiving portion for receiving one branch of a Y-site.

13. The system of claim 12 wherein the receiving portion comprises a slot for receiving at least a portion of the one branch of the Y-site.

14. The system according to claim 4 wherein the sterile cover is retained in a first package, the device further comprising disinfectant within the first package.

15. The system according to claim 4 wherein the sterile cover is retained in a first package, the device further comprising a swab retained adjacent the sterile cover.

16. The system according to claim 15 further comprising a second package adjacent the first package and wherein the swab is contained within the second package.

17. The system according to claim 16 wherein the second package is mounted with the first package.

18. The system according to claim 16 wherein the second package is connected with the first package.

19. The system according to claim 16 further comprising a disinfectant along the sterile cover and/or the swab.

20. The system according to claim 16 further comprising a disinfectant along both the sterile cover and the swab, the disinfectant along the sterile cover being a chemically different disinfectant than the disinfectant along the swab.

* * * * *